(12) United States Patent
Kuroda et al.

(10) Patent No.: US 7,563,452 B2
(45) Date of Patent: Jul. 21, 2009

(54) COSMETIC

(75) Inventors: Akihiro Kuroda, Kanagawa (JP); Koji Sakuta, Gunma (JP); Hitoshi Usui, Tokyo (JP)

(73) Assignees: Kanebo Cosmetics Inc., Tokyo (JP); Shin-Etsu Chemical Co., Ltd., Tokyo (JP)

(*) Notice: Subject to any disclaimer, the term of this patent is extended or adjusted under 35 U.S.C. 154(b) by 169 days.

(21) Appl. No.: 11/506,170

(22) Filed: Aug. 17, 2006

(65) Prior Publication Data

US 2006/0280712 A1    Dec. 14, 2006

Related U.S. Application Data

(63) Continuation of application No. 10/070,601, filed as application No. PCT/JP00/05838 on Aug. 29, 2000, now abandoned.

(30) Foreign Application Priority Data

Aug. 30, 1999  (JP)  ................... 11-242948
Aug. 30, 1999  (JP)  ................... 11-242949
Sep. 21, 1999  (JP)  ................... 11-266824

(51) Int. Cl.
*A61K 8/02*    (2006.01)
*B60C 1/00*    (2006.01)

(52) U.S. Cl. ...................... 424/401; 524/261

(58) Field of Classification Search .............. 424/401; 524/261

See application file for complete search history.

(56) References Cited

U.S. PATENT DOCUMENTS 4,970,252 A * 11/1990 Sakuta et al. ............... 524/268
5,061,481 A * 10/1991 Suzuki et al. ................ 424/63
5,236,986 A *  8/1993 Sakuta ....................... 524/267
5,496,544 A *  3/1996 Mellul et al. ............ 424/78.03
5,853,711 A * 12/1998 Nakamura et al. ....... 424/78.03

* cited by examiner

*Primary Examiner*—Gina C. Yu
(74) *Attorney, Agent, or Firm*—Birch, Stewart, Kolasch & Birch, LLP

(57) ABSTRACT

The present invention is a cosmetic, characterized in that it contains an organopolysiloxane having the following general formula:

$$\{(CH_3)_3SiO\}_3SiCH_3 \quad (1)$$

The cosmetic demonstrates excellent volatility and feel when used, and excellent storage stability.

20 Claims, No Drawings

COSMETIC

CROSS REFERENCE TO RELATED APPLICATIONS:

This application is a continuation application of U.S. Ser. No. 10/070,601 filed Feb. 28, 2002 now abandoned. U.S. Ser. No. 10/070,601 is a national stage application of PCT/JP00/05838 with an international filing date of Aug. 29, 2000. Both applications are herein incorporated by reference.

FIELD OF THE TECHNOLOGY

The present invention relates to a cosmetic containing a specific organopolysiloxane. More precisely, it relates to a cosmetic showing excellent feel to the touch when applied and longer lasting cosmetic coverage, which contains a volatile branched organopolysiloxane having a specific structure exhibiting a high volatility.

BACKGROUND OF THE INVENTION

Volatile cyclic silicones which are disclosed in Japanese Patent Nos. 2517311, 2525193, 2843266, 2934773, 2967141, and 3020716 have been widely used in water-in-oil type emulsions and oil-based cosmetics.

Generally, human secretions such as sweat, tears and sebum cause makeup runs. Specially, in makeup cosmetics, an oil agent contained in cosmetics along with sebum secreted from the skin causes excessive wetting of cosmetic powder, which results in serious makeup runs. In order to reduce the amount of cosmetic oil remaining on the skin, an attempt was made to use a volatile oil such as octamethylcyclotetrasiloxane or decamethylcyclopentasiloxane as a part of the oil ingredients to be added.

Water is also an external factor causing poor coverage with cosmetics. In order to improve such poor makeup coverage caused by substances soluble in sweat or water, or to maintain a protective effect on the skin by preventing loss of water-soluble components from the skin, silicone oil was added to increase water repellency. Since silicone oil represented by dimethylpolysiloxane demonstrates superior features such as light to the touch, excellent water repellency, and high safety when applied, it has been used as an oil agent in cosmetics along with a volatile silicone.

However, since octamethylcyclotetrasiloxane which is a volatile silicone (hereinafter referred to as D4) has a solidification point of 17° C., D4 in a product containing D4 crystallizes in winter to cause separation in the product. In addition, when manufacturing such a product in winter, D4 must be dissolved once by heating prior to its addition, which is a source of concern in the manufacturing process.

Since decamethylcyclopentasiloxane (hereinafter referred to as D5) has a solidification point of −40° C., the above-mentioned problem does not occur. However, since its boiling point is so high as 210° C., it lacks volatility, so that there is a problem with sensory features if D4 is replaced with D5. Another problem therein is that as D5 remains on the skin for a longer time, strength of the cosmetic film is weaker, so that the duration of the cosmetic coverage is reduced. For this reason, D4 and D5 were mostly used together in practice to attain volatility and prevention of crystallization together.

On the other hand, as disclosed in Japanese Kokai (Laid-Open) Patent No. 9-175940, it is known to blend a solution of a silicone resin (trimethylsiloxysilicate) in D5 to sunscreen agents and cosmetic foundations. In this case, it is also known that the duration of the cosmetic coverage is improved on account of the addition of a silicone resin solution. However, the reality was that when the effect of a silicone resin solution was tested both in model experiments and in actual applications, the effect achieved in the actual applications was not so high as the effect achieved in the model experiments. The reason for this seems that D5 does not vaporize and remains on the skin, so that the effect of the silicone resin is not exhibited.

DISCLOSURE OF THE INVENTION

The inventors have earnestly investigated the subject of concern in an attempt to solve the various problems as described above and have now discovered the fact that a volatile branched organopolysiloxane having a specific structure has excellent volatility and therefore, unlike D5, does not remain on the skin for a long time and it does not crystallize in winter, unlike D4; it has no safety problem and; it barely defats the skin. This organopolysiloxane has a boiling point of 190° C., which is close to that of D4, and however its solidification point is −82.8° C., so that it does not crystallize in winter unlike D4. In addition, the organopolysiloxane demonstrates a high applicability as an oil agent for cosmetics and, moreover, the cosmetics containing the organopolysiloxane give a feel of lightness without a feel of dryness caused by conventional cyclic silicones.

The present invention is a cosmetic wherein the cosmetic contains an organopolysiloxane having the following general formula (1)

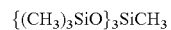  (1)

The present invention is the cosmetic wherein it further contains at least one other kind of organopolysiloxane than that of the formula (1).

Preferred embodiments of the present invention include the following.

The cosmetic wherein the other kind of organopolysiloxane is liquid at 25° C. and 1 atm.

The cosmetic wherein said liquid organopolysiloxane is volatile at 25° C. and 1 atm.

The cosmetic wherein said volatile organopolysiloxane is a cyclic dimethylpolysiloxane having 4 to 6 silicon atoms.

The cosmetic wherein said liquid organopolysiloxane is non-volatile at 25° C. and 1 atm.

The cosmetic wherein said non-volatile organopolysiloxane is at least one selected from the group consisting of dimethylpolysiloxanes and methylphenylpolysiloxanes.

The cosmetic wherein said other kind of organopolysiloxane is of a paste, gum, elastomeric solid or non-elastomeric solid form at 25° C. and 1 atm.

The cosmetic wherein said gum form of organopolysiloxane is dimethylpolysiloxane gum with a degree of polymerization ranging from 3,000 to 20,000.

The cosmetic wherein said elastomeric solid form or non-elastomeric solid form of organopolysiloxane is dispersed in the cosmetic.

The cosmetic wherein said non-elastomeric solid form of organopolysiloxane is polyalkylsilsesquioxane spherical powder.

The cosmetic wherein said non-elastomeric solid form of organopolysiloxane is at least one selected from the group consisting of acrylic silicone copolymers, fluorinated organopolysiloxanes, trimethylsiloxysilicates (i.e., MQ resins), and trimethylsiloxysilicates containing a dimethylsiloxy group (i.e., MDQ resins).

The cosmetic wherein said other kind of organopolysiloxane is a modified organopolysiloxane.

The cosmetic wherein said modified organopolysiloxane is at least one selected from the group consisting of fluorinated organopolysiloxanes, polyether-modified organopolysiloxanes, amino-modified organopolysiloxanes, organopolysiloxanes containing an alcoholic hydroxyl group, glyceryl-modified organopolysiloxanes, and polyglyceryl-modified organopolysiloxanes.

The cosmetic wherein said other kind of organopolysiloxanes is a crosslinked organopolysiloxane.

The cosmetic wherein said crosslinked organopolysiloxane is a reaction product of organopolysiloxane having at least two alkenyl groups per molecule with organohydrogenpolysiloxane having a Si—H bond.

The cosmetic wherein said crosslinked organopolysiloxane has at least one moiety selected from the group consisting of polyoxyalkylene moieties, alkyl moieties, alkenyl moieties, and aryl moieties.

The cosmetic wherein said crosslinked organopolysiloxane is present, in the cosmetic, in a swollen state in an organopolysiloxane with a dynamic viscosity of 0.65 to 100 mm$^2$/s.

The cosmetic wherein it further contains a fluorine-containing compound.

The cosmetic wherein it further contains a UV-ray protective component.

The cosmetic wherein said UV-ray protective component is at least one selected from the group consisting of fine particle titanium dioxide, fine particle zinc oxide, 2-ethylhexyl paramethoxycinnamate, 4-tert-butyl-4'-methoxydibenzoylmethane, and benzophenone UV-ray absorbents.

The cosmetic wherein it further contains a compound having an alcoholic hydroxyl group.

The cosmetic wherein it further contains a thickening agent.

DESCRIPTION OF THE PREFERRED EMBODIMENTS

The volatile branched organopolysiloxane used in this invention (hereinafter referred to as M3T) is expressed by the following general formula:

$$\{(CH_3)_3SiO\}_3SiCH_3 \quad (1)$$

M3T is a compound which was investigated in the Soviet Union during the 1970's. For example, see Dokl. Akad. Nauk SSSR Vol. 227 (3), pp. 607-610 (1976).

However, use of M3T in cosmetics is not known. All patents concerning cosmetics containing volatile silicone concern silicones derived from cyclic, straight chain or phenyl groups, but no patents mention M3T.

M3T may be prepared in any known method. For example, it can be obtained by co-hydrolysis of methyltrichlorosilane and trimethylchlorosilane. For a molar ratio, at least 3 mols of trimethylchlorosilane are needed per mol of methyltrichlorosilane.

M3T can also be obtained by hydrolysis of hexamethyldisiloxane and methyltrialkoxysilane in the presence of an acidic catalyst. As the methyltrialkoxysilanes, methyltrimethoxysilane, methyltriethoxysilane, methyltripropoxysilane, and methyltributoxysilane are desirable. Examples of the acidic catalyst include sulfuric acid, methanesulfonic acid, trifluoromethanesulfonic acid, and ion exchange resins, and the reaction is carried out using a solvent such as ethanol and isopropylalcohol. Regarding the molar ratio, at least 1.5 mols of hexamethyldisiolxane are needed per mol of methyltrialkoxysilane.

In addition, M3T can also be obtained by an XY-elimination reaction between $(CH_3)_3SiOSi(X)CH_3Si(CH_3)_3$ and $CH_3SiY$, wherein X and Y are groups selected from the group consisting of hydrogen, chlorine, and alkoxy groups.

It is desirable to use M3T purified to a lead level of 20 ppm or less, and an arsenic level of 2 ppm or less from the standpoint of human safety, and an amount of contaminating components having one silicon atom to 0.1 mass % or less. Examples of the contaminating components containing one silicon atom include $(CH_3)_3SiCl$, $(CH_3)_3SiOH$, and $(CH_3)_3SiH$. All of these compounds are strongly irritating to the skin, so that their addition to cosmetics is not desirable. Since straight chain or cyclic compounds containing two or three silicon atoms are also strongly irritating to the skin, they are not desirable, either.

In the present invention, M3T may be added to the cosmetics arbitrarily in the range of from 0.1 to 99.9 mass %. The blend concentration of M3T may be determined depending on a combination with the other kind of organopolysiloxanes than M3T and a form of the cosmetics, as will be described below.

In the cosmetic of the present invention, it is desirable to use M3T in combination with the other kind of organopolysiloxanes which have been used in cosmetics (hereinafter, sometimes, referred to as "silicone compound"). Examples of the other kind of organopolysiloxanes include organopolysiloxanes and modified organopolysiloxanes which are, at 25° C. and 1 atm, of a volatile or non-volatile liquid form, a paste form, i.e., an intermediate state between a liquid form and a solid form, a gum form, i.e., showing plasticity, which is not crosslinked or slightly crosslinked, an elastomeric solid (elastomer) form, a non-elastomeric solid form, a solution of a solid, and powder form. Specifically, those described in "Standards for Cosmetic Ingredients" and "Japanese Cosmetic Ingredients Codex" are included. M3T demonstrates excellent compatibility with these organopolysiloxanes.

In the present invention, the liquid organopolysiloxanes which are volatile at 25° C. and 1 atm (volatile silicone) are those having a boiling point of 300° C. or less, preferably 250° C. or less, at 1 atm. Examples of such include linear or cyclic polysiloxanes which contain 3 to 7 silicon atoms and have a methyl-, ethyl-, phenyl-, and/or trifluoropropyl group, preferably cyclic dimethylpolysiloxanes having 4 to 6 silicon atoms and linear dimethylpolysiloxanes having 4 to 5 silicon atoms. The aforementioned cyclic dimethylpolysiloxanes include octamethylcyclotetrasiloxane, decamethylcyclopentasiloxane, and dodecamethylcyclohexasiloxane. By the use of these conventional volatile silicones together with M3T, the vaporization speed can be controlled or sensory features can be modified. The mixing mass ratio of M3T to these volatile silicones may be in a range of from 99:1 to 1:99. However, in particular, a range of from 10:90 to 95:5 is desirable since the effect of the addition of M3T is more prominent.

The liquid organopolysiloxanes which are non-volatile at 25° C. at 1 atm include nonvolatile dimethylpolysiloxane and methylphenylpolysiloxane. In particular, those with a degree of polymerization ranging from 10 to less than 3,000, preferably with a dynamic viscosity ranging from 6 to 1,000,000 cs(mm$^2$/s) are desirable. For example, products under the tradenames of KF96 and KF54 are commercially available from Shin-Etsu Chemical Co., Ltd.

M3T is also suitable as a solvent for dissolving, swelling or dispersing organopolysiloxanes which are of paste form, gum form, elastomeric solid form (elastomer) or non-elastomeric solid form at 25° C. and at 1 atm.

The gum form organopolysiloxanes include substituted or unsubstituted organopolysiloxanes having RRSiO units, e.g., dimethylpolysiloxane, methylphenylpolysiloxane, and methylfloroalkylpolysiloxane, or those having a slightly crosslinked structure. In particular, dimethylpolysiloxane gum with a degree of polymerization ranging from 3,000 to 20,000 is desirable. The gum form organopolysiloxane may be dissolved in a solvent containing M3T, or it may be dispersed along with M3T in water, a polyhydric alcohol or a fluoric oil agent using a surfactant. In this case, the dispersion particle size is not particularly limited, but a range of from 1 nm to 50 µm is desirable.

The elastomeric solid (elastomer) form organopolysiloxanes include crosslinked organopolysiloxanes as described below. The elastomeric solid form organopolysiloxane is added to the cosmetic, for example, in a powder form. In this case, a desirable form of powder is spherical ones or aggregates thereof.

The non-elastomeric solid form organopolysiloxanes include those which are commonly called silicone resin compounds, for example, those expressed by the average formula: $R_n SiO_{(4-n)/2}$ and having $RRRSiO_{0.5}$ units (i.e., M units), RRSiO units (i.e., D units), $RSiO_{1.5}$ units (i.e., T units), and $SiO_2$ units (i.e. Q units), wherein the average number of n ranges preferably from 1 to 1.8. In the formula, R preferably represents a substituted or unsubstituted linear or branched alkyl group having 1 to 30 carbon atoms, or an organic residue having a phenyl group, amino group, polyether group, glycoside derivatives, glyceryl group, or polyglyceryl group, and all of the R groups may be identical or different.

In addition, the other silicone resin compounds include silicone-modified pullulans (e.g., trimethylsilyl pullulan such as silylated polymer L-MPL, produced by Shin-Etsu Chemical Co., Ltd.) and acrylic silicone copolymer resins. Among them all, preferred in particular are acrylic silicone copolymer resins, fluorine-modified silicone resins, trimethylsiloxysilicate (i.e., MQ resins), and trimethylsiloxysilicate containing a dimethylsiloxy group (i.e., MDQ resins) due to their excellent applicability.

The aforementioned acrylic silicone copolymer resins include acrylic/silicone graft or block copolymers. In particular, silicone copolymer compounds containing at least one moiety selected from the group consisting of pyrrolidone moieties, long-chain alkyl moieties, polyoxyalkylene moieties, fluoroalkyl moieties, and amino moieties are desirable since they improve duration of the cosmetic coverage. Examples of the acrylic silicone copolymer resins are KP545 and KP561, produced by Shin-Etsu Chemical Co., Ltd.

Another type of the non-elastometic solid form organopolysiloxanes includes polyalkylsilsesquioxanes such as polymethylsilsesquioxane (i.e., T resins, wherein alkyl groups are substituted or unsubstituted alkyl groups having 1 to 30 carbon atoms). In particular, a spherical form having a primary particle size ranging from 0.1 to 20 µm, preferably from 1 to 7 µm, is desirable. The polyalkylsilsesquioxane may be a spherical silicone resin powder such as KMP590 produced by Shin-Etsu Chemical CO., Ltd.

M3T is characteristic in that if the gum form, elastomeric solid form or non-elastomeric solid form organopolysiloxane is dissolved in M3T, the film completion rate becomes faster due to the high volatization rate of M3T, so that durability of the cosmetic is improved. M3T is also excellent as a swelling or dispersing medium so that it is suitable for blending an insoluble organopolysiloxane powder to cosmetics. The mixing ratio of M3T to the gum form, elastomer form, or non-elastomeric solid form of organopolysiloxane ranges preferably from 99:1 to 20:80, more preferably from 85:15 to 40:60, when no other solvent is used. These organopolysiloxanes are preferably dissolved or dispersed in a solvent containing M3T prior to the addition to the cosmetics.

To blend the aforementioned non-volatile liquid form, paste form, elastomeric solid form or non-elastomeric solid form of organopolysiloxanes to the cosmetics, a desirable amount thereof ranges from 0.01 to 80 mass %, relative to the total amount of the cosmetic.

In the cosmetic of the present invention, it is desirable to use M3T together with a modified organopolysiloxane since this improves sensory features of the modified organopolysiloxane, especially, reduces an oily feel. The modified organopolysiloxanes include those than obtained by substituting the methyl group or the like in common organopolysiloxanes such as dimethylorganopolysiloxane and methylphenylpolysiloxane with another organic group. For example, the following compounds are desirable: fluorine-modified organopolysiloxanes, polyether-modified organopolysiloxanes, amino-modified organopolysiloxanes, organopolysiloxanes containing an alcoholic hydroxyl group, glyceryl-modified organopolysiloxanes, polyglyceryl-modified organopolysiloxanes, sugar-modified organopolysiloxanes, organopolysiloxanes modified with an alkyl group other than methyl or phenyl, and amodimethicones. In particular, fluorine-modified organopolysiloxanes, polyether-modified organopolysiloxanes, amino-modified organopolysiloxanes, organopolysiloxanes containing an alcoholic hydroxyl group, glyceryl-modified organopolysiloxanes, and polyglyceryl-modified organopolysiloxanes are desirable. It is effective to use one or more kinds of these compounds in combination since an effect of improvement by M3T in the feel to the touch can be felt readily.

A desirable amount of the modified organopolysiloxane to be added to the cosmetic ranges from 0.01 to 80 mass %, relative to the total amount of the cosmetic. The mixing mass ratio of the modified organopolysiloxane to M3T may be set arbitrarily in a range of from 0.1:99.9 to 99.9:0.1, preferably in a range of from 5:95 to 99:1.

M3T demonstrates an excellent compatibility with those which act as a surfactant among the modified organopolysiloxanes (i.e., silicone surfactant). Therefore, M3T can be advantageously added to an emulsion containing such a silicone surfactant. Examples of the modified organopolysiloxanes which can act as a surfactant include those having at least one kind of a modifying group selected from the group consisting of polyoxyalkylene groups, partially substituted or unsubstituted alkyl groups having 2 to 30 carbon atoms, alcoholic hydroxyl groups, phenyl groups, glyceryl groups, saccharide residues, oxazoline groups, and perfluoropolyether, bonded to a dimethylsiloxane chain, and also having a modifying pendant or terminal group or block unit containing a hydrophilic group, such as polyoxyalkylene groups, glyceryl groups, saccharide residues, perfluoropolyether groups, and alcoholic hydroxyl groups, as an essential constituent. For example, the following compounds may be used: polyether-modified organopolysiloxanes (also called polyoxyalkylene-modified silicones, polyether-modified silicones, or polyether-modified siloxanes), alkyl/polyoxyalkylene-comodified silicones (also called polyetheralkyl-comodified siloxanes), fluorinated dimethiconols, perfluoroalkyl/polyoxyalkylene-comodified silicones, perfluoroalkoxy/polyoxyalkylene-comodified silicones, glyceryl-modified silicones, perfluoroalkyl/polyglyceryl-comodified silicones, and glycosyl-modified silicones. Among these silicone surfactants, ones having an HLB ranging from 1 to 12 are desirable due to their excellent compatibility with M3T, and those having an HLB ranging from 1 to 9 are most desirable.

Examples of such polyether-modified organopolysiloxanes include KF6012, KF6015, KF6017, KF6026, and FPD6131, produced by Shin-Etsu Chemical Co., Ltd.

A desirable amount of the silicone surfactant to be added ranges from 0.1 to 20 mass %, preferably from 0.5 to 10 mass % relative to the total amount of the cosmetic.

In the present invention, a crosslinked organopolysiloxane is preferably used in combination with M3T since it improves the feel to the touch of the cosmetic. The crosslinked organopolysiloxane has an elastomer form or a non-elastomeric form, depending upon the degree of crosslinking and so on. A reaction product of an organopolysiloxane having two or more alkenyl groups per molecule with an organohydrogenpolysiloxane having a SiH bond is desirable as the crosslinked organopolysiloxanes. Alternatively, crosslinked organopolysiloxanes having at least one moiety selected from the group consisting of polyoxyalkylene moieties, alkyl moieties, alkenyl moieties, and aryl moieties are preferably used. Crosslinked organopolysiloxanes which have been swollen in advance in a low-viscosity organopolysiloxane in an amount exceeding the amount of the crosslinked organopolysiloxane may be used. This low-viscosity organopolysiloxane may be such with a viscosity (dynamic viscosity) of 0.65 to 100 $mm^2/s$ at 25° C. An example of the crosslinked organopolysiloxanes containing a low-viscosity organopolysiloxane is the KSG series produced by Shin-Etsu Chemical Co., Ltd.

The aforementioned crosslinked organopolysiloxane may be added to the cosmetic in a powder form or a paste form. For a particle size, those with a primary particle size ranging from 0.1 to 50 μm are desirable. As examples of the spherical ones, MP594 and the KSP series by Shin-Etsu Chemical Co., Ltd. may be named. The surface of the crosslinked polymer of the KSP series is coated with a silsesquioxane. Aggregates of the spherical ones are also preferred. A desirable amount of the crosslinked organopolysiloxane to be added to the cosmetic ranges from 0.01 to 50 mass % relative to the total amount of the cosmetic.

The cosmetic of the present invention preferably contains a fluorine-containing compound in addition to the aforementioned organopolysiloxane. In general, fluorine-containing compounds are water repellant and oil repellant, so that they are known to be poorly compatible with other oils. For this reason, fluorine surfactants containing fluorine atoms in the molecule, e.g., perfluoroalkyl/polyoxyalkylene-comodified silicones and perfluoroalkyl/polyglyceryl-comodified silicones were developed. M3T demonstrates excellent compatibility with these surfactants. M3T is also a low surface tension liquid and, therefore, shows excellent compatibility also with many fluorine-containing compound.

The fluorine-containing compound may be of a liquid form, a paste form or a solid form at 25° C. and at 1 atm. Besides the aforementioned fluorine surfactant, other fluorine-containing compounds may be used, such as fluorine-modified silicones, perfluoropolyethers, fluorinated pitch, perfluorodecaline, fluorocarbons such as perfluorooctane, fluoroalcohols, and perfluoroalkylalkylethers. In particular, fluorine-modified silicones, perfluoroalkylbiphenyl-modified silicones, and perfluoropolyethers are desirable since they can be used for many purposes. When the fluorine-containing compound is added to the cosmetic of the present invention, its desirable amount ranges from 0.01 to 60 mass %, preferably from 0.3 to 15 mass %, relative to the total amount of the cosmetic.

The cosmetic of the present invention preferably contains a UV-ray protective component in addition to the aforementioned components. The UV-ray protective component is removed by sweat, water or sebum with time to loose its effect. For this reason, an attempt has been made to maintain the effect by using the aforementioned conventional silicone compounds or fluorine-containing compounds in the formulization. However, if D5, for instance, is added, its volatility is poor and it does not vaporize quickly even in summer, so that a cosmetic film is not completed, resulting in shorter duration of the UV-ray protection effect. In contrast, M3T has a high volatility and forms a cosmetic film quickly, so that it has a significant effect on improvement in the duration of cosmetic coverage. Therefore, the combination of M3T with a UV-ray protective component is highly effective. In particular, the combination of a silicone resin compound with a UV-ray protective component and M3T is desirable.

In the present invention, inorganic and organic UV-ray protection agents may be used as the UV-ray protective component. Examples of the inorganic ones include metal oxides such as titanium dioxide, titanium monoxide, zinc oxide, and cerium oxide, metal hydroxides such as iron hydroxide, tabular iron oxide, metal flakes such as aluminum flakes, and ceramics such as silicon carbide. In particular, it is desirable to use at least one kind selected from fine particle metal oxides or fine particle metal hydroxides with a mean particle size ranging from 5 to 100 nm. Those particles are preferably surface-treated in a conventional method, e.g., treatment with a fluorine compound, preferably perfluoroalkylphosphate, perfluoroalkylsilane, perfluoropolyether, fluorosilicone, and fluorinated silicone resin, treatment with silicone, e.g., methylhydrogenpolysiloxane, dimethylpolysiloxane, or vapor phase treatment with tetramethyltetrahydrogen cyclotetrasiloxane, pendant treatments, i.e., addition of an alkyl chain after vapor phase treatment with silicone, treatment with a silane coupling agent, treatment with a titanium coupling agent, treatment with silane, preferably alkylsilane or alkylsilazane, treatment with an oil agent, treatment with N-acylated lysine, treatment with polyacrylic acid, treatment with a metal soap, preferably stearic acid or myristic acid salts, treatment with an acrylic resin, and treatment with metal oxide. It is more desirable to apply a combination of plural treatments selected from the aforementioned treatments. For example, the surface of fine particle titanium dioxide is coated with a metal oxide such as silicon oxide or alumina and subsequently surface-treated with an alkylsilane. The total amount of the surface treatment is preferably from 0.1 to 50 mass %, relative to the mass of the powder.

Examples of the organic UV-ray protection agents are as follows: 2-ethylhexyl paramethoxycinnamate (also called octyl paramethoxycinnamate), 2-hydroxy-4-methoxybenzophenone, 2-hydroxy-4-methoxybenzophenone-5-sulfuric acid, 2,2'-dihydroxy-4-methoxybenzophenone, p-methoxyhydrocinnamic acid diethanolamine salt, paraaminobenzoic acid (hereinafter referred to as PABA), ethyldihydroxypropyl PABA, glyceryl PABA, homomenthyl salicylate, methyl-O-aminobenzoate, 2-ethylhexyl-2-cyano-3,3-diphenylacrylate, octyldimethyl PABA, octyl salicylate, 2-phenyl-benzimidazole-5-sulfuric acid, triethanolamine salicylate, 3-(4-methylbenzylidene)camphor, 2,4-dihydroxybenzophenine, 2,2',4,4'-tetrahydroxybenzophenone, 2,2'-dihydroxy-4,4-dimethoxybenzophenone, 2-hydroxy-4-N-octoxybenzophenone, 4-isopropyl dibenzoylmethane, 4-tert-butyl-4'-methoxydibenzoylmethane, octyltriazone, 2-ethylhexyl 4-(3,4-dimethoxyphenylmethylene)-2,5-dioxo-1-imidazolidine propionate, polymer derivatives thereof, and silane derivatives thereof.

It is also possible to use an organic UV-ray protection agent encapsulated in polymer powder. The polymer powder may be hollow or not, a mean primary particle size may be in a range of 0.1 to 50 μm, and the particle distribution may be broad or sharp. Types of the polymer include acrylic resins, methacrylic resins, styrene resins, polyurethane resins, polyethylenes, polypropylenes, polyethylene terephthalates, silicone resins, nylons, and acrylamide resins. The organic UV-ray protection agent is preferably incorporated in the polymer powder in a range from 0.1 to 30 mass % relative to the powder mass. In particular, it is desirable to use 4-tert-butyl-4'-methoxydibenzoylmethane which is a UVA absorbent.

Among the aforementioned UV-ray protective components, use is preferably made of at least one selected from the group consisting of fine particle titanium dioxide, fine particle zinc oxide, 2-ethylhexyl paramethoxycinnamate, 4-tert-butyl-4'-methoxydibenzoylmethane, and UV absorbents of the benzophenone series, because these are widely used and can be obtained easily and their UV protection effect is high. In particular, it is preferred to use an inorganic one and an organic one in combination. It is also preferred to use a combination of one for UV-A with one for UV-B.

A desirable amount of the UV-ray protective component as a sum of inorganic and organic ones in the cosmetic of the present invention ranges from 0.1 to 60 mass %, preferably from 3 to 40 mass % relative to the cosmetic.

The cosmetic of the present invention preferably contains a compound having an alcoholic hydroxyl group in the molecular structure in addition to the aforementioned various components. Generally, when a compound having an alcoholic hydroxyl group except lower alcohols is mixed in a cosmetic, one often feels tackiness and stickiness while drying after the cosmetic is applied on the skin. It was desired to eliminate these features by formulation. M3T has an effect of reducing the aforementioned stickiness while drying after the application of a cosmetic. Accordingly, use of M3T together with a compound having an alcoholic hydroxyl group demonstrates a high sensory effect.

The compound having an alcoholic hydroxyl group according to the present invention is preferably selected from monohydric alcohols, polyhydric alcohols, sterols, sugars, sugar alcohols and sugar derivatives. In particular, it is preferred to use one or more of monohydric alcohols, polyhydric alcohols, sugars, and sugar alcohols. Specific examples of these compounds are described below and they can be used alone or in combination.

Examples of the alcohol include lower alcohols such as ethanol, propanol, and isopropanol; sugar alcohols such as sorbitol, maltose, and maltitol; sterols such as cholesterol, sitosterol, phytosterol, and lanosterol; glucose, sucrose, lactose, raffinose, trehalose, xylitol, glycerin, propylene glycol, dipropylene glycol, tripropylene glycol, polypropylene glycol, 1,3-butylene glycol, ethylene glycol, diethylene glycol, triethylene glycol, polyglycerin, hyaluronic acid and its salts, chondroitin sulfuric acid and its salts, pyrrolidone carboxylic acid salts, polyoxyethylene methylglucoside, polyoxypropylene methylglucoside, and ethylglucoside.

A desirable amount of the compound having an alcoholic hydroxyl group in the cosmetic of the present invention ranges from 0.01 to 95 mass %, preferably from 0.1 to 50 mass %.

In addition, M3T used in the present invention exhibits a similar sensory effect on a thickening agent as on the compounds having an alcoholic hydroxyl group. The following compounds are used as the thickening agent: plant-derived polymers such as gum Arabic, tragacanth gum, arabinogalactan, locust bean gum (carob gum), guar gum, karaya gum, carrageenan, pectin, agar-agar, quince seed (i.e., marmelo), starch from rice, corn, potato or wheat, algae colloid, and trant gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyethylene glycol; polyoxyethylene/polyoxypropylene copolymers; acrylic polymers such as sodium polyacrylate, polyethyl acrylate, and polyacrylamide; polyethyleneimine; cationic polymers; and inorganic thickening agents such as, bentonite, aluminum magnesium silicate, laponite, smectite, saponite, hectorite, and silicic anhydride.

An oil-soluble gelling agent may also be used as the thickening agent. For example, at least one may be selected from the following group: metal soaps such as aluminum stearate, magnesium stearate, and zinc myristate; α amino acid derivatives such as N-lauroyl-L-glutamic acid, α, γ-di-n-butylamine; dextrin fatty acid esters such as dextrin palmitate, dextrin stearate, and dextrin 2-ethylhexane palmitate; sucrose fatty acid esters such as sucrose palmitate and sucrose stearate; benzylidene derivatives of sorbitol such as monobenzylidene sorbitol and dibenzylidene sorbitol; clay minerals modified with an organic moiety such as dimethylbenzyldodecylammonium montmorillonite clay, dimethyldioctadecylammonium montmorillonite, and octadecyldimethylbenzylammonium montmorillonite.

A desirable amount of the thickening agent in the cosmetic of the present invention ranges from 0.01 to 95 mass %, preferably from 0.1 to 50 mass %, relative to the cosmetic.

Moreover, the cosmetic of the present invention may preferably contain one or more kinds of components selected from powder and coloring agents along with the aforementioned components. One of the problems in cosmetics containing powder or coloring agents is noticeable cosmetic run in general. The powder and coloring agents are fixed on the skin by an oil agent or a resin which is called binder. If a volatile solvent or the like remains on the skin, a film is not formed very quickly, which is one of the causes for cosmetic run. As M3T has an appropriately high volatility, M3T does not cause wrinkling or run while applying the cosmetic or touching up the cosmetic and, after the application of the cosmetic, M3T vaporizes quickly. Accordingly, it is desirable to blend M3T to the cosmetic containing powder and coloring agents.

Any powder and coloring agents which are commonly used in cosmetics may be used in the present invention, regardless of the shape (spherical, rod-like, acicular, tubular, irregular, scaly or spindle forms), particle size (size of hume, fine particles or pigment grade), and particle structure (porous and non-porous), such as, for example, inorganic powder, organic powder, surface active, metal salt powder, colored pigments, pearl pigments, metallic powder pigments, and natural colors. Specific examples include inorganic powder, such as titanium oxide, zirconium oxide, zinc oxide, cerium oxide, magnesium oxide, barium sulfate, calcium sulfate, magnesium sulfate, calcium carbonate, magnesium carbonate, talc, mica, kaolin, cericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolite, zeolite, ceramics powder, calcium secondary phosphate, alumina, aluminum hydroxide, boron nitride, and silica; organic powder such as polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose, silk powder, nylon powder such as Nylon 12 and Nylon 6, acrylic powder, acrylic elastomer, styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fiber powder, starch powder, and lauroyl lysine; surface active metal salt powders (metal soaps) such as zinc stearate, aluminum stearate, calcium stearate, magnesium stearate, zinc myristate, magnesium myristate, zinc cetyl phosphate, calcium cetyl phosphate, and zinc/sodium cetyl phosphate; colored pigments including inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder complexes thereof; pearl pigments such as titanium oxide-coated mica, titanium oxide-coated mica, bismuth oxychloride, titanium oxide-coated bismuth oxychloride, titanium oxide-coated talc, fish scales, and titanium oxide-coated colored mica; metallic powder pigments such as aluminum powder, copper powder and stainless powder; tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin. These powders can be compounded or can be treated with common oil agents, silicone oil, fluorine-containing compounds and surfactants as far as the effect of the present invention is not prevented, as described above. For example, these powders may be or may not be surface-treated or modified in advance by, for example, the treatment with a fluorine-containing compound, treatment with a silicone resin, pendant treatment, treatment with a silane coupling agent, treatment with a titanium coupling agent, treatment with an oil agent, treatment with N-acylated lysine, treatment with a polyacrylic acid, treatment with a metal soap, treatment with an amino acid, treatment with an inorganic compound, plasma treatment, and mechanochemical treatment. If necessary, one or more kinds of surface treatments or modification can be applied. According to the present invention, one or more kinds of the powders may be combined.

The amount of the powder and/or pigment to be blended in the present cosmetic is typically 0.1 to 99 mass %, preferably 1 to 70 mass %, depending much upon a form of the cosmetic.

In the cosmetic of the present invention, a variety of components that are commonly used in cosmetics can be blended in addition to the aforementioned components, as far as the purpose of the present invention is not damaged, for example, oil agents, surfactants, antiseptics, perfumes, humectants, salts, solvents, antioxidants, chelating agents, neutralizers, pH regulators, insect repellants, and bioactive components.

Examples of the oil agents are as follows: avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil; hydrocarbon oils, e.g., ozokerite, squalane, squalene, ceresin, paraffin, paraffin wax, liquid paraffin, pristane, polyisobutylene, microcrystalline wax, and Vaseline; higher fatty acids, e.g., lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid; higher alcohols, e.g., lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol); ester oils, e.g., diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate; and glyceride oils, e.g., acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Known surfactants include anionic, cationic, nonionic and amphoteric surfactants, but are not particularly limited to these. Any of those which are commonly used in cosmetics may be used. Specific examples are as follows: anionic surfactants including fatty acid soaps, such as sodium stearate and triethanolamine palmitate, alkylether carboxylic acids and salts thereof, carboxylates of condensates from amino acids and fatty acids, alkyl sulfonic acids, alkenesulfonates, fatty acid ester sulfonates, fatty acid amide sulfonates, sulfonate salts of the formalin condensates with alkyl sulfonates, salts of sulfate esters such as salts of alkyl sulfates, salts of secondary higher alcohol sulfates, salts of alkyl/allyl ether sulfates, salts of fatty acid ester sulfates, salts of fatty acid alkylolamide sulfates, and Turkey Red oil, alkyl phosphates, ether phosphates, alkylallylether phosphates, amide phosphates, and N-acylamino surfactants; cationic surfactants including amine salts such as alkylamine salts, polyamine and amino alcohol fatty acid derivatives, alkyl quaternary ammonium salts, aromatic quaternary ammonium salts, pyridium salts and imidazolium salts; nonionic surfactants including sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkylethers, polyoxypropylene alkylethers, polyoxyethylene alkylphenylether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanolether, polyoxyethylene phytosterolether, polyoxyethylene cholestanolether, polyoxyethylene cholesterylether, alkanolamide, sugar ethers, and sugar amides; and amphoteric surfactants including betaine, aminocarboxylates, and imidazoline derivatives. A desirable amount of the surfactant to be added ranges from 0.1 to 20 mass %, preferably from 0.5 to 10 mass % relative to the total amount of the cosmetic. One or more kinds of the surfactants may be used.

For the antiseptics, alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide, triclosan, photosensitizer and phenoxyethanol.

The bioactive components used in the present invention include materials which impart certain bioactivities to the skin when applied on the skin. For example, the following agents are used: anti-inflammatory agents, anti-aging agents, UV protection agents, astringents, antioxidants, hair growth stimulants, hair restoration tonics, humectants, blood circulation promoters, antibacterial agents, drying agents, cooling agents, thermal agents, vitamins, amino acids, wound healing promoters, anti-irritants, painkillers, cellular activators, and enzyme components. In particular, plant extracts, seaweed extracts, and herbal components from natural sources are desirable. In the present invention, one or more kinds of these bioactive components may preferably be added.

Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric[Curcuma] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscus tea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, Saponaria extract, Bamboo extract, Crataegus fruit extract, Zanthoxylum fruit extract, shiitake extract, Rehmannia root extract, gromwell extract, Perilla extract, linden extract, Filipendula extract, peony extract, Calamus Root extract, white birch extract, Horsetail extract, Hedera Helix(Ivy) extract, hawthorn extract, Sambucus nigra extract, Achillea millefolium extract, Mentha piperita extract, sage extract, mallow extract, Cnidium officinale Root extract, Japanese green gentian extract, soybean extract, jujube extract, thyme extract, tea extract, clove extract, Gramineae imperata cyrillo extract, Citrus unshiu peel extract, Japanese Angellica Root extract, Calendula extract, Peach Kernel extract, Bitter orange peel extract, Houttuyna cordata extract, tomato extract, natto extract, Ginseng extract, garlic extract, wild rose extract, hibiscus extract, Ophiopogon tuber extarct, Nelumbo nucifera extract, parsley extract, honey, hamamelis extract, Parietaria extract, Isodonis herba extract, bisabolol extract, Loquat extract, coltsfoot extract, butterbur extract, Porid cocos wolf extract, extract of butcher's broom, grape extract, propolis extract, luffa extract, safflower extract, peppermint extract, linden tree extract, Paeonia extract, hop extract, pine tree extract, horse chestnut extract, Mizu-bashou [*Lysichiton camtschatcese*] extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

Further examples of the bioactive components include the following groups: biopolymers such as deoxyribonucleic acid, mucopolysaccharides, sodium hyarulonate, sodium chondroitin sulfate, collagen, elastin, chitin, chitosan, and hydrolyzed chorionic membrane; amino acids such as glycine, valine, leucine, isoleucine, serine, threonine, phenylalanine, arginine, lysine, aspatic acid, glutamic acid, cystine, cysteine, methionine, and tryptophan; hormones such as estradiol and ethenylestradiol; moisturizing components such as amino acids, sodium lactate, urea, sodium pyrrolidonecarboxylate, betaine, and whey; oily components such as sphingolipids, ceramide, cholesterol, cholesterol derivatives, and phospholipids; anti-inflammatory agents such as $\epsilon$-aminocapronic acid, glycyrrhizic acid, $\beta$-glycyrrhetic acid, lysozyme chloride, guaiazulene, hydrocortisone, arantoin, tranexamic acid, and azulene; vitamins such as vitamin A, B2, B6, C, D, E, calcium pantothenate, biotin, nicotinic amide, and vitamin C ester; active components such as arantoin, diisopropylamine dichloroacetate, and 4-aminomethylcyclohexanoic acid; antioxidants such as tocopherol, carotinoide, flavonoid, tannin, lignan, saponin, butylhydroxyanisole, dibutylhydroxytoluene, and phytin; cellular activators such as $\alpha$-hydroxy acid, $\beta$-hydroxy acid; blood circulation promoters such as $\gamma$-oryzanol and vitamin E derivatives; wound healing promoters such as retinol and retinol derivatives; refrigerants such as cepharantine, Glycyrrhiza extract, cayenne pepper tincture, hinokitiol, iodized garlic extract, pyridoxine hydrochloride, dl-$\alpha$-tocopherol, dl-$\alpha$-tocopherol acetic acid, nicotinic acid, nicotinic acid derivatives, calcium pantothenate, D-pantothenyl alcohol, acetyl pantothenyl ethylether, biotin, arantoin, isopropylmethylphenol, estradiol, ethinyl estradiol, carpronium chloride, benzalkonium chloride, diphenhydramine hydrochloride, tacanal, camphor, salicylic acid, nonylic acid vanillylamide, nonanoic acid vanillylamide, pirocton olamin, glyceryl pentadecanoate, 1-menthol, and camphor; hair restorers such as mononitro guaiacol, resolcinol, γ-aminobutylic acid, benzethonium chloride, mexiletine hydrochloride, auxin, female hormones, cantharis tincture, cyclosporin, zinc pyrithione, hydrocortisone, minoxyzil, polyoxyethylenesorbitan monostearate, peppermint oil, and sasanishiki extract.

Examples of the pH regulator include lactic acid, citric acid, glycolic acid, succinic acid, oxalic acid, dl-malic acid, calcium carbonate, sodium hydrogen carbonate, and ammonium hydrogen carbonate. Examples of the chelating agent include alanine, sodium edetate, sodium polyphosphate, sodium methaphosphate, and phosphoric acid.

Examples of the solvent to be used include light isoparaffin, ethers, LPG, N-methylpyrrolidone, and next-generation Flon besides purified water and mineral water.

Usages of the cosmetic of the present invention are not particularly limited. The following usages are most desirable: skin care products, hair care products, antiperspirant products, makeup products, UV-ray protection products, and perfumes. Examples of these usages include basic cosmetics such as milky lotions, creams, lotions, calamine lotions, sunscreen agents, sun tanning agents, aftershave lotions, preshave lotions, facial pack formulas, cleansing products, facial washes, acne remedy cosmetics, and essences; makeup cosmetics such as foundation, face powder, eye shadow, eyeliner, eyebrow, cheek, nail colors, lip cream, and lipstick; shampoos, rinses, conditioners, hair colors, hair tonics, hair-setting agents, body powder, hair restorers, deodorants, hair removers, soaps, body shampoos, bath agents, hand soaps, and perfumes.

The forms of the products are not particularly limited. Any forms can be selected, such as liquid form, milky liquid form, cream form, solid form, paste form, gel form, powder form, multiphase form, moose form, and spray form. Particularly preferred are emulsion type, multiphase dispersion type, gel or spray formulations in which M3T and water are blended.

EXAMPLES

The present invention will be further explained in detail below by referring to the Examples and the Comparative Examples. However, the present invention shall not be limited to these examples. "%" described below implies "% by mass" unless otherwise specified.

Preparation 1 of M3T 1800 g of water and 200 g of methanol were placed in a reactor. While the reactor was cooled with ice with stirring, a mixture of 420 g of trimethylchlorosilane and 150 g of methyltrichlorosilane was added dropwise to carry out hydrolysis. At the end of the addition, the reaction mixture was maintained for 2 hours. After cooling and removing acid wastes, the product was washed with water and neutralized. The product was dried by adding anhydrous sodium sulfate and M3T was obtained by distillation. Its boiling point was 73 to 74° C./20 mmHg and a yield was 93 g (percent yield: 30%).

Preparation 2 of M3T 136 g of methyltrimethoxysilane, 324 g of hexamethyldisiloxane and 64 g of methanol were placed in a reactor. While cooling the reactor with ice, 10 g of concentrated sulfuric acid was added with stirring. A mixture of 32.4 g of water and 32.4 g of methanol was added dropwise to carry out hydrolysis. At the end of the addition, the mixture was maintained for 30 min. and then the catalyst and the alcohol were removed by washing with water. The product was dried by adding anhydrous sodium sulfate and M3T was obtained by distillation. Its boiling point was 73 to 74° C./20 mmHg and the yield was 216 g (percent yield: 70%).

M3T prepared in one of the aforementioned methods was analyzed by gas chromatography and its purity was found to be 99.3%. The structure was identified by $^{29}$Si—NMR (3Si at δ5 to 10 ppm and 1Si at δ−60 to −70 ppm, TMS standard) and mass spectrometry (molecular ion peak: 310).

Example 1

UV-Ray Protection Cosmetic Base

A solution dissolving trimethylsiloxysilicate, a kind of silicone resin compound, at a concentration of 50% by mass in M3T was prepared and a UV-ray protection cosmetic base was prepared according to the formulation shown in the table below.

|  | % |
|---|---|
| (Component A) | |
| (1) Silicone-treated fine particle titanium dioxide | 4 |
| (2) M3T | 10 |
| (3) KF6017 | 1 |
| (Component B) | |
| (4) Silicone-treated fine particle zinc oxide | 6 |
| (5) Perfluoroalkylphosphate-treated colored skin-color mica | 0.5 |
| (Component C) | |
| (6) Crosslinked organopolysiloxane spherical powder (Elastomer) | 4 |
| (7) Dimethylpolysiloxane (KF96A-6) | 2 |
| (8) Fluorinated dimethiconol | 1 |
| (9) M3T | 15 |
| (10) Trimethylsiloxysilicate solution | 6 |
| (11) Octyl paramethoxycinnamate | 3 |
| (12) Perfluoropolyether | 0.5 |
| (Component D) | |
| (13) Ethyl alcohol | 10 |
| (14) Purified water | Balance |
| (15) *Aloe* extract | 1 |
| (16) *Hamamelis* extract | 1 |
| (17) *Hibiscus* extract | 0.5 |

KF6017 (produced by Shin-Etsu Chemical Co., Ltd.): Polyoxyethylene/methylpolysiloxane copolymer (HLB = 4.6)

KF96A-6 (produced by Shin-Etsu Chemical Co., Ltd.): Dimethylpolysiloxane with viscosity of 6 mm$^2$/s (Preparation Method)

Step 1: Component A was around with a roller mill to form a paste.

Step 2: Component C was simply mixed and ground with a mixer.

Step 3: After mixing Component B with Component C to be dispersed, Component A was added thereto and mixed well.

Step 4: After adding and stirring Component D which has been made into a homogeneous solution, the mixture was packed together with stainless balls in a container to obtain a product.

Example 2

A product was obtained in the same method as in Example 1 except that D4 was used instead of M3T in Component A in the Table shown in Example 1 above.

Comparative Example 1

A product was obtained in the same method as in Example 1 except that D5 was used instead of all of M3T in the Table shown in Example 1 above.

Comparative Example 2

A product was obtained in the same method as in Example 1 except that D5 was used instead of M3T in a trimethylsiloxysilicate solution, i.e., Component C, and D5 was used instead of M3T in Component A in the Table shown in Example 1 above.

The following evaluation tests were conducted on the products obtained in Examples 1 and 2, and in Comparative Examples 1 and 2.

[Evaluation of Sensory Features and Evaluation of Durability of the Cosmetic Coverage]

Sensory features of the trial products were evaluated by 10 special panelists. For each sensory feature, a product showing an excellent result was graded as point +5 and a product showing a poor result was graded as point 0. A product indicating a result in between these was assessed into four levels. A total score from all the panelists was the final evaluation. Therefore, a higher score implies higher evaluation. The durability of the cosmetic coverage was assessed as follows. After the cosmetic base obtained in one of the Examples was applied on one half of the face and that obtained in one of the Comparative Examples on the other half of the face, a commercial summer foundation was applied on the top and the duration of the cosmetic coverage was evaluated in the same assessment method as above.

The results of evaluation are as shown in the Table below. According to the test results, the Examples of the present invention demonstrate a longer lasting cosmetic coverage and a refreshing feel with a less oily feel when applied and thereafter. Regarding the durability of the cosmetic coverage by the products of the Example, the makeup run due to sebum is less. In addition, no abnormalities were detected on the skin in all of the cases after the samples were used.

|  | Volatile silicone in Component A | Volatile silicone in Component C | Durability of cosmetic coverage | Refreshing feel |
| --- | --- | --- | --- | --- |
| Example 1 | M3T | M3T | 42 | 39 |
| Example 2 | D4 | M3T | 44 | 40 |
| Comp. Ex. 1 | D5 | D5 | 29 | 16 |
| Comp. Ex. 2 | D4 | D5 | 32 | 22 |

Comp. Ex.: Comparative Example

Examples 3, 4, and 5

Whitening Cream for Daytime Use

A whitening cream was prepared in the formulation shown below.

|  | Example No. | | |
| --- | --- | --- | --- |
|  | 3 | 4 | 5 |
|  | (%) | | |
| (Component A) | | | |
| (1) KF6017 | 1 | 1 | 1 |
| (2) KF6026 | — | — | 2 |
| (3) KF56 | 5 | 5 | 5 |
| (4) KF995 | 12 | 3 | — |
| (5) M3T | 10 | 19 | 12 |
| (Component B) | | | |
| (6) Glycerin | 5 | 5 | 5 |
| (7) Dipropylene glycol | 10 | 10 | 10 |
| (8) Methyl paraoxybenzoate | 0.2 | 0.2 | 0.2 |
| (9) Sodium ascorbyl sulfate | 0.1 | 0.1 | 0.1 |
| (10) Sodium ascorbyl phosphate | 0.1 | 0.1 | 0.1 |
| (11) γ-amino butyric acid | 0.1 | 0.1 | 0.1 |
| (12) Apple seed kernel extract (antioxidant) | 0.1 | 0.1 | 0.1 |
| (13) Sodium chloride | 0.9 | 0.9 | 0.9 |
| (14) Perfume | 0.1 | 0.1 | 0.1 |
| (15) Purified water | Balance | Balance | Balance |

KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)
KF56 (produced by Shin-Etsu Chemical Co., Ltd.): Methylphenylpolysiloxane
KF995 (produced by Shin-Etsu Chemical Co., Ltd.): Decamethylcyclopentasiloxane (D5)

(Preparation Method)
Step 1: Component A was dissolved by heating at 60° C.
Step 2: Component B was dissolved by heating at 60° C.
Step 3: Component A was added to Component B while stirring to form an emulsion.
Step 4: Subsequently, the mixture was cooled to 30° C. while stirring and packed in a container to obtain a product.

Comparative Example 3

A product was obtained in the same method as in Example 4 except that D4 was used instead of M3T in Example 4.

Comparative Example 4

A product was obtained in the same method as in Example 5 except that D4 was used instead of M3T in Example 5. The following evaluation tests were conducted on the products obtained in Examples 3 through 5 and Comparative Examples 3 and 4.

[Evaluation of Sensory Features and Evaluation of Durability of the Cosmetic Coverage]

Sensory features of the trial products were evaluated by 10 special panelists. A product showing an excellent result on sensory feature on questionnaire whether the feel to the touch was smooth or not was graded as point +5 and a product showing a poor result was graded as point 0, whereas one indicating a result in between these was assessed into four levels. A total score from all of the panelists was the final scores of evaluation. Therefore, a higher score implies higher evaluation. The low-temperature stability was investigated as follows. Samples were stored at 0° C. and returned to room temperature. Then, it was observed by the naked eye whether the separation in the products occurred or not.

The results of the evaluation are as shown in the Table below. According to the test results, the Examples of the present invention demonstrate superior low-temperature stability, compared to the Comparative Examples, and feel to the touch similar to or slightly better than the formulation using D4. Additionally, satisfactory results were obtained such that the prior silicone emulsification technique can be applied as such, the D5 can be used together and then, a dry feel is reduced compared to D4. No abnormalities were detected on the skin after all the samples were used.

| Example No. | Low-temperature stability test | Smooth feel to the touch |
| --- | --- | --- |
| Example 3 | No problem | 43 |
| Example 4 | No problem | 44 |
| Example 5 | No problem | 42 |
| Comparative Example 3 | Slightly separated | 41 |
| Comparative Example 4 | Separated | 39 |

Example 6

Sunscreen Agent

A sunscreen agent was prepared based on the formulation described below. The UV-ray protective components used were 2-ethylhexyl paramethoxycinnamate, treated fine particle titanium dioxide, treated fine particle zinc oxide, and treated yellow fine particle titanium dioxide. As a silicone resin compound, trimethylsiloxysilicate was used.

For the treated fine particle titanium dioxide, fine particle titanium dioxide with a mean particle size of 17 nm coated with silica/alumina was coated with octyltrimethoxysilane in an amount of coating of 8 wt % and heat treated at 160° C. For the treated fine particle zinc oxide, fine particle zinc oxide with a mean particle size of 50 nm treated with silica was coated with methylhydrogenpolysiloxane in an amount of coating of 3 wt % and heat treated at 170° C. For the treated yellow fine particle titanium dioxide, iron-doped fine particle titanium dioxide treated with silica was coated with methylhydrogenpolysiloxane in an amount of coating of 3 wt % and heat treated at 130° C.

|  | (%) |
| --- | --- |
| Component A | |
| Treated fine particle titanium dioxide | 8.0 |
| M3T | 12.0 |
| Component B | |
| Treated yellow fine particle titanium dioxide | 0.8 |
| Treated fine particle zinc oxide | 17.0 |
| Component C | |
| Three-dimensionally crosslinked organopolysiloxane spherical powder (Elastomer) | 1.0 |
| Dimethiconol | 6.0 |
| M3T | 17.0 |
| Trimethylsiloxysilicate | 6.0 |
| 2-ethylhexyl paramethoxycinnamate | 10.0 |

-continued

|  | (%) |
| --- | --- |
| Component D | |
| Ethyl alcohol | 5.0 |
| Purified water | Balance |
| *Aloe* extract | 0.5 |

Component A was ground with a roller mill to form a paste. Component C was simply mixed and thoroughly ground with a mixer. After mixing Component B with Component C to be thoroughly dispersed, Component A was added and the mixture was further mixed well. Subsequently, Component D, which had been dissolved homogeneously, was added and stirred thoroughly, and then the mixture was packed with stainless balls in a container.

Comparative Example 5

A product was obtained in the same method as in Example 6 except that D4 was used instead of M3T used in Example 6.

Comparative Example 6

A product was obtained in the same method as in Example 6 except that D5 was used instead of M3T used in Example 6.

[Evaluation of Sensory Features]

Sensory features of the products were evaluated by 10 special panelists. A product showing an excellent result on each sensory feature on a questionnaire whether the UV-ray protection effect lasted long or not and whether the feel to the touch was smooth or not was graded as point +5 and a product showing a poor result was graded as point 0, whereas one indicating a result in between these was assessed into four levels. A total score from all of the panelists is the final evaluation. Therefore, a higher score implies higher evaluation. The low-temperature stability was investigated as follows.

[Low-temperature Stability Test]

When a product was placed in a thermostatic chamber at 0° C., occurrence of crystallization in the formulation was observed by the naked eye.

|  | Long lasting effect | Good feel to the touch | Low-temperature stability test |
| --- | --- | --- | --- |
| Example 6 | 44 | 42 | No problem |
| Comp. Ex. 5 | 45 | 43 | A problem detected (Crystallization) |
| Comp. Ex. 6 | 38 | 30 | No problem |

According to the test results mentioned above, the Examples of the present invention were superior to the Comparative Examples.

Comparative Example 5 was the case using D4 instead of M3T. The product was highly volatile and demonstrated excellent durability of the UV-ray protection effect, but D4 crystallized at a low temperature. Therefore, it is concluded that the product was not suitable for winter use. In Comparative Example 6 where D5 was used instead of M3T, an oily feel to the touch was found, which is an issue of concern. In contrast, the product obtained in Example 6 demonstrated excellent overall results in a feel to the touch, durability of the effect and stability of the formulation. In addition, the addition of M3T caused no problem with safety to human skin.

Example 7

Sunscreen Agent (Cream)

| (Components) | (%) |
|---|---|
| 1. M3T | 20.0 |
| 2. Liquid paraffin | 10.0 |
| 3. KF6017 | 1.9 |
| 4. KF6026 | 4.0 |
| 5. 4-t-butyl-4'-methoxydibenzoylmethane | 7.0 |
| 6. Distearyldimethylammonium chloride | 0.8 |
| 7. Vitamin E acetate | 0.1 |
| 8. Ethanol | 1.0 |
| 9. Sumectite | 1.2 |
| 10. Antiseptic | Proper quantity |
| 11. Perfume | Proper quantity |
| 12. Purified water | Balance |

KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)

(Preparation Method)
A: Components 1 through 7 and 10 were mixed while heating.
B: Components 8, 9 and 12 were heated and mixed to be dispersed homogeneously.
C: While stirring, B was added portionwise to A to emulsify and, after cooling, Component 11 was added to obtain a sunscreen agent (cream).

The sunscreen agent (cream) thus obtained was evenly applicable, non-sticky so as not to attract sand, gave a silky finish, and demonstrated superior user satisfaction. The cosmetic coverage lasted long, so that the effect of UV-ray protection continued long. No change was found with temperature change or with time, showing superior stability.

Example 8

Sunscreen Agent (Cream)

| (Components) | (%) |
|---|---|
| 1. M3T | 18.0 |
| 2. KF56 | 2.0 |
| 3. Liquid paraffin | 1.5 |
| 4. KF6012 | 4.0 |
| 5. Octyl paramethoxycinnamate | 5.0 |
| 6. 1,3-butylene glycol | 4.0 |
| 7. Sodium chloride | 1.0 |
| 8. Antiseptic | Proper quantity |
| 9. Perfume | Proper quantity |
| 10. Purified water | Balance |

KF56 (produced by Shin-Etsu Chemical Co., Ltd.): Methylphenylpolysiloxane
KF6012 (produced by Shin-Etsu Chemical Co., Ltd): Polyoxyethylene/polyoxypropylene/methylpolysiloxane copolymer (HLB = 7.0)

(Preparation Method)
A: Components 1-5 were mixed while heating.
B: Components 6-8 and 10 were heated to be dissolved.
C: While stirring, B was added portionwise to A to emulsify and, after cooling, Component 9 was added to obtain a sunscreen agent (cream).

The sunscreen agent (cream) thus obtained was evenly applicable, moisturizing, had a silky finish, and gave very good user satisfaction. It maintained long lasting cosmetic coverage with excellent waterproofing and sweat resistance, so that the effect of UV-ray protection continued long. No change was found with temperature change or with time, showing superior stability.

Example 9

Sunscreen Agent (Cream)

| (Components) | (%) |
|---|---|
| 1. M3T | 17.5 |
| 2. KP545 | 12.0 |
| 3. Glycerol triisooctanoate | 5.0 |
| 4. Octyl paramethoxycinnamate | 6.0 |
| 5. KSG21 | 5.0 |
| 6. KF6017 | 1.0 |
| 7. Lipophilic-treated zinc oxide | 20.0 |
| 8. Sodium chloride | 0.5 |
| 9. 1,3-butylene glycol | 2.0 |
| 10. Antiseptic | Proper quantity |
| 11. Perfume | Proper quantity |
| 12. Purified water | Balance |

KP545 (produced by Shin-Etsu Chemical Co., Ltd.): Acrylic silicone polymer resin/decamethylcyclopentasiloxane 30% solution
KSG21 (produced by Shin-Etsu Chemical Co., Ltd.): Crosslinked polyether-modified methylpolysiloxane/dimethylpolysiloxane
KF6017 (produced by Shin-Etsu Chemical Co., Ltd.): Polyoxyethylene/methylpolysiloxane copolymer (HLB = 4.6)

(Preparation Method)
A: Component 2 was added to a portion of Component 1 to obtain a homogeneous mixture and then Component 7 was added to be dispersed with a beads mill.
B: The remaining portion of Component 1 and Components 3-6 were mixed homogeneously.
C: Components 8-10 and Component 12 were mixed to be dissolved.
D: C was added to B to emulsify, and A and Component 11 were added to obtain a sun blocking cream.

The sunscreen agent (cream) thus obtained was non-sticky, evenly applicable, well suited for the skin, and presented a glossy finish. The cosmetic coverage lasted long. It was very stable to temperature change or with time.

Example 10

Sunscreen Agent (Astringent)

| (Components) | (%) |
|---|---|
| 1. M3T | 14.0 |
| 2. KF615A | 10.0 |
| 3. Squalane | 1.5 |

-continued

| (Components) | (%) |
|---|---|
| 4. Octyl paramethoxycinnamate | 3.0 |
| 5. Titanium TTO-S2 | 2.0 |
| 6. 1,3-butylene glycol | 10.0 |
| 7. Sodium chloride | 2.0 |
| 8. L-proline | 0.1 |
| 9. 2-hydroxyoctanoic acid | 1.0 |
| 10. 2-hydroxypropanoic acid | 5.0 |
| 11. Sodium hydroxide | Proper quantity |
| 12. Antiseptic | Proper quantity |
| 13. Perfume | Proper quantity |
| 14. Purified water | Balance |

KF615A (produced by Shin-Etsu Chemical Co., Ltd.): Polyoxyethylene/polyoxypropylene/methylpolysiloxane copolymer (HLB = 14.0)
Titanium TTO-S2 (produced by Sakai Chemical Co., Ltd.): Ultra-fine particle titanium dioxide treated for hydrophobicity (Preparation Method)
A: Components 6-14 were dissolved homogeneously.
B: Components 1-4 were mixed and Component 5 was added to obtain a homogeneous mixture.
C: While stirring, B was added portionwise to A to emulsify to obtain a sun blocking astringent.

The sunscreen agent (astringent) thus obtained was evenly applicable, moisturizing, well suited for the skin, and gave a refreshing feel to users. It had a superior effect of preventing suntan. No change was found with temperature change or with time, showing superior stability.

Example 11

Sunscreen Agent (Milky Lotion)

| (Components) | (%) |
|---|---|
| 1. M3T | 25.0 |
| 2. Diglyceryl monoisostearate | 1.5 |
| 3. Decaglyceryl pentaisostearate | 1.5 |
| 4. KF6012 | 0.5 |
| 5. Olive oil | 1.0 |
| 6. Fine particle titanium dioxide | 7.0 |
| 7. Glycerin | 5.0 |
| 8. Sodium chloride | 1.5 |
| 9. Antiseptic | Proper quantity |
| 10. Perfume | Proper quantity |
| 11. Purified water | Balance |

KF6012 (produced by Shin-Etsu Chemical Co., Ltd): Polyoxyethylene/polyoxypropylene/methylpolysiloxane copolymer (HLB = 7.0)

(Preparation Method)
A: Components 1-5 were mixed while heating and Component 6 was dispersed homogeneously.
B: Components 7-9 and Component 11 were mixed while heating.
C: While stirring, B was added portionwise to A to emulsify and, after cooling, Component 10 was added to obtained a sunscreen agent (milky lotion).

The sunscreen agent (milky lotion) thus obtained was less viscous, of fine silky texture, evenly applicable, and non-sticky to give good user satisfaction. With the long lasting cosmetic coverage, the effect of UV-ray protection continued long. The stability of powder dispersion and emulsification was excellent with temperature change or with time.

Example 12

Sunscreen Agent (Milky Lotion)

| (Components) | (%) |
|---|---|
| 1. M3T | 20.0 |
| 2. KF56 | 3.0 |
| 3. Sorbitan monoisostearate | 1.0 |
| 4. KF6012 | 0.5 |
| 5. Silicone resin | 1.0 |
| 6. Octyl paramethoxycinnamate | 4.0 |
| 7. Fine particle titanium dioxide | 8.0 |
| 8. Sorbitol | 2.0 |
| 9. Sodium chloride | 2.0 |
| 10. Antiseptic | Proper quantity |
| 11. Perfume | Proper quantity |
| 12. Purified water | Balance |

KF56 (produced by Shin-Etsu Chemical Co., Ltd.): Methylphenylpolysiloxane
Silicon resin: 50% solution, in M3T, of a silicone network compound (trimethylsiloxysilicate) with a ratio, $[Me_3SiO_{1/2}]/[SiO_2]$, of 0.8
KF6012 (produced by Shin-Etsu Chemical Co., Ltd): Polyoxyethylene/polyoxypropylene/methylpolysiloxane copolymer (HLB = 7.0)

(Preparation Method)
A: Components 1-6 were mixed while heating and Component 7 was dispersed homogeneously.
B: Components 8-10 and Component 12 were mixed while heating.
C: While stirring, B was added portionwise to A to emulsify and, after cooling, Component 11 was added to obtained a sunscreen agent (milky lotion).

The sunscreen agent (milky lotion) thus obtained was evenly applicable, moisturizing and presented a fine silky look. With the long lasting cosmetic coverage, the effect of UV-ray protection continued long. No change was found with temperature change or with time, showing superior stability.

Example 13

Suntan Cream

| (Components) | (%) |
|---|---|
| 1. M3T | 15.0 |
| 2. KF96A-100 | 5.0 |
| 3. KP-562 | 0.5 |
| 4. KF6017 | 2.2 |
| 5. KF6026 | 6.0 |
| 6. Palmitic acid | 0.2 |
| 7. Dimethyloctyl paraaminobenzoic acid | 0.5 |
| 8. 4-t-butyl-4'-methoxy-dibenzoylmethane | 0.5 |
| 9. Kaolin | 0.5 |
| 10. Iron oxide red | 0.2 |
| 11. Iron oxide yellow | 0.3 |
| 12. Iron oxide black | 0.1 |
| 13. Titanium oxide coated mica | 1.0 |
| 14. Sodium L-glutamate | 3.0 |

-continued

| (Components) | (%) |
|---|---|
| 15. 1,3-butylene glycol | 5.0 |
| 16. Dioctadecyldimethyl ammonium chloride | 0.1 |
| 17. Antioxidant | Proper quantity |
| 18. Antiseptic | Proper quantity |
| 19. Perfume | Proper quantity |
| 20. Purified water | Balance |

K96F-100 (produced by Shin-Etsu Chemical Co., Ltd.): Dimethylpolysiloxane with a viscosity of 100 mm$^2$/s
KP-562 (produced by Shin-Etsu Chemical Co., Ltd.): Behenyl-modified acrylic silicone graft copolymer
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)

(Preparation Method)

A: Components 1-8 and Components 17-18 were dissolved by heating.

B: After stirring Component 16 and a portion of Component 20 while heating, Components 9-13 were added to disperse.

C: Components 14-15 and the remaining portion of Component 20 were dissolved homogeneously and combined with B.

D. While stirring, C was added portionwise to A to emulsify and, after cooling, Component 19 was added to obtain a suntan cream.

The suntan cream thus obtained was evenly applicable, moisturizing, well suited feel for the skin, and gave a fine silky look and a refreshing feel to users. The cosmetic coverage lasted long. Neither separation nor coagulation of the powder was found with temperature change or with time, showing superior stability.

Example 14

Foundation

| (Components) | (%) |
|---|---|
| 1. M3T | 45.0 |
| 2. KF96A-6 | 5.0 |
| 3. KF6017 | 1.5 |
| 4. KF6026 | 0.5 |
| 5. Montmorillonite modified by octadecyldimethylbenzylammonium | 4.0 |
| 6. Titanium dioxide treated for hydrophobicity* | 10.0 |
| 7. Talc treated for hydrophobicity* | 6.0 |
| 8. Mica treated for hydrophobicity* | 6.0 |
| 9. Iron oxide red* treated for hydrophobicity | 1.6 |
| 10. Iron oxide yellow* treated for hydrophobicity | 0.7 |
| 11. Iron oxide black* treated for hydrophobicity | 0.2 |
| 12. Dipropylene glycol | 5.0 |
| 13. Methyl paraoxybenzoate | 0.3 |
| 14. 2-amino-2-methyl-1,3-propanediol | 0.2 |
| 15. Hydrochloric acid | 0.1 |

-continued

| (Components) | (%) |
|---|---|
| 16. Perfume | Proper quantity |
| 17. Water | Balance |

K96F-100 (produced by Shin-Etsu Chemical Co., Ltd.): Dimethylpolysiloxane with a viscosity of 100 mm$^2$/s
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)
*Treatment for hydrophobicity: after adding 2% of methylhydrogenpolysiloxane to the powder, a heat treatment was applied.

(Preparation Method)

A: Components 1-5 were mixed while heating and Components 6-11 were added to obtain a homogeneous mixture.

B: Components 12-15 and Component 17 were dissolved by heating (pH of the aqueous system: 9.0).

C. While stirring, B was added portionwise to A to emulsify and, after cooling, Component 16 was added to obtain a foundation.

The foundation thus obtained was evenly applicable, moisturizing, of a fine silky texture and gave a refreshing feel to users. The cosmetic coverage lasted long. No change was found with temperature change or with time, showing superior stability.

Example 15

Foundation

| (Components) | (%) |
|---|---|
| 1. KF96A-6 | 5.0 |
| 2. M3T | 15.0 |
| 3. Squalane | 4.0 |
| 4. Neopentyl glycol dioctanoate | 3.0 |
| 5. Myristic acid isostearic acid diglyceride | 2.0 |
| 6. α-monoisostearyl glycerylether | 1.0 |
| 7. KF6015 | 1.0 |
| 8. Aluminum distearate | 0.2 |
| 9. Titanium dioxide treated for hydrophobicity* | 5.0 |
| 10. Cerisite treated for hydrophobicity* | 2.0 |
| 11. Talc treated for hydrophobicity* | 3.0 |
| 12. Iron oxide red treated for hydrophobicity* | 0.4 |
| 13. Iron oxide yellow treated for hydrophobicity* | 0.7 |
| 14. Iron oxide black treated for hydrophobicity* | 0.1 |
| 15. Magnesium sulfate | 0.7 |
| 16. Glycerin | 3.0 |
| 17. Antiseptic | Proper quantity |
| 18. Perfume | Proper quantity |
| 19. Purified water | Balance |

KF6017 (produced by Shin-Etsu Chemical Co., Ltd.): Polyoxyethylene/methylpolysiloxane copolymer (HLB = 4.6)
*Hydrophobic powder: powder was treated with 2%, based on the powder, of stearic acid.

(Preparation Method)

A: Components 1-8 were mixed while heating and Components 9-14 were added to obtain a homogeneous mixture.

B: Components 15-17 and Component 19 were dissolved by heating.

C. While stirring, B was added portionwise to A to emulsify and, after cooling, Component 18 was added to obtain a foundation.

The foundation thus obtained was less viscous, evenly applicable, moisturizing, and gave a fine silky look and a refreshing feel to users. The cosmetic coverage lasted long. No change was found with temperature change or with time, showing superior stability.

Example 16

Foundation

| (Components) | (%) |
|---|---|
| 1. M3T | 18.0 |
| 2. KF56 | 5.0 |
| 3. Sorbitan monoisostearate | 0.5 |
| 4. Diglyceryl monoisostearate | 0.5 |
| 5. KF6012 | 1.0 |
| 6. Octyl paramethoxycinnamate | 3.0 |
| 7. Titanium oxide | 10.0 |
| 8. Iron oxide red | 0.13 |
| 9. Iron oxide yellow | 0.3 |
| 10. Iron oxide black | 0.07 |
| 11. Talc | 2.5 |
| 12. Sorbitol | 2.0 |
| 13. Magnesium sulfate | 0.1 |
| 14. Ethanol | 10.0 |
| 15. Antiseptic | Proper quantity |
| 16. Perfume | Proper quantity |
| 17. Purified water | Balance |

KF56 (produced by Shin-Etsu Chemical Co., Ltd.): Methylphenylpolysiloxane
KF6012 (produced by Shin-Etsu Chemical Co., Ltd): Polyoxyethylene/polyoxypropylene/methylpolysiloxane copolymer (HLB = 7.0)

(Preparation Method)
A: Components 7-11 were mixed homogeneously.
B: Components 1-6 and Component 15 were mixed while heating and A was added to obtain a homogeneous dispersion.
C. Components 12-13 and Component 17 were heated and added to B to emulsify and, after cooling, Components 14 and 16 were added to obtain a foundation.

The foundation thus obtained was non-sticky, evenly applicable, and gave a refreshing feel to users. It was in a good emulsion state and less affected with temperature changes, and showed no separation or aggregation with time, showing superior stability.

Example 17

Foundation

| (Components) | (%) |
|---|---|
| 1. M3T | 15.0 |
| 2. KF96A-6 | 5.0 |
| 3. Liquid paraffin | 3.0 |
| 4. KF6015 | 3.0 |
| 5. Palmitic acid | 0.5 |
| 6. Aerosil RY200 | 5.0 |
| 7. Titanium dioxide | 6.0 |
| 8. Iron oxide red | 0.25 |
| 10. Iron oxide yellow | 0.6 |
| 11. Iron oxide black | 0.12 |
| 12. Cerisite | 8.03 |

-continued

| (Components) | (%) |
|---|---|
| 13. Dipropylene glycol | 10.0 |
| 14. Magnesium sulfate | 2.0 |
| 15. Antiseptic | Proper quantity |
| 16. Antioxidant | Proper quantity |
| 17. Perfume | Proper quantity |
| 18. Purified water | Balance |

KF96A-6 (produced by Shin-Etsu Chemical Co., Ltd.): Dimethylpolysiloxane with a viscosity of 6 mm$^2$/s
KF6015 (produced by Shin-Etsu Chemical Co., Ltd.): Polyoxyethylene/methylpolysiloxane copolymer (HLB = 4.5)
Aerosil RY200 (produced by Nippon Aerosil Co., Ltd.): Hydrophobic silica (Preparation Method)
A: Components 8-12 were mixed homogeneously.
B: Components 1-7 and Component 16 were mixed and heated to 70° C. under stirring, to which A was added to obtain a homogeneous dispersion.
C. Components 13-18 were heated to 70° C. and added to B to emulsify and, after cooling, Component 17 was added to obtain a foundation.

The foundation thus obtained was non-sticky, evenly applicable, and gave a refreshing and cool feel to users. It was in a good emulsion state and demonstrated long lasting cosmetic coverage and was less affected with temperature change, showing superior stability with time.

Example 18

Foundation

| (Components) | (%) |
|---|---|
| 1. M3T | 16.0 |
| 2. KF96A-6 | 8.0 |
| 3. Octyl paramethoxycinnamate | 3.0 |
| 4. 12-hydroxysteatic acid | 1.0 |
| 5. FL-100 | 15.0 |
| 6. FPD-6131 | 5.0 |
| 7. KMP590 | 3.0 |
| 8. Fine particle titanium dioxide treated with a fluorine compound* | 8.0 |
| 9. mica titanium treated with a fluorine compound* | 1.0 |
| 10. Titanium dioxide treated with a fluorine compound* | 5.0 |
| 11. Iron oxide red treated with a fluorine compound* | 0.9 |
| 12. Iron oxide yellow treated with a fluorine compound* | 2.0 |
| 13. Iron oxide black treated with a fluorine compound* | 1.0 |
| 14. Ethanol | 15.0 |
| 15. Glycerin | 3.0 |
| 16. Magnesium sulfate | 1.0 |
| 17. Antiseptic | Proper quantity |

| (Components) | (%) |
|---|---|
| 18. Perfume | Proper quantity |
| 19. Purified water | Balance |

KF96A-6 (produced by Shin-Etsu Chemical Co., Ltd.): Dimethylpolysiloxane with a viscosity of 6 mm$^2$/s
FL-100 (produced by Shin-Etsu Chemical Co., Ltd.): Trifluoropropylmethylsilicone
FPD6131 (produced by Shin-Etsu Chemical Co., Ltd.): Polyoxyethylene/trifluorpropyl/methylpolysiloxane copolymer (HLB = 5.4)
KMP590 (produced by Shin-Etsu Chemical Co., Ltd.): Spherical silicone resin powder
*Treatment with a fluorine compound: coated with 5% of perfluoroalkylethylphosphate diethanolamine salt (Preparation Method)
A: Components 7-13 were mixed homogeneously.
B: Components 1-6 were mixed while heating to 70° C. and A was added to obtain a homogeneous dispersion.
C. Components 14-17 and Component 19 were heated to 40° C. and added portionwise to B to emulsify. After cooling, Component 18 was added to obtain a liquid foundation.

The foundation thus obtained was non-sticky, evenly applicable, and gave a refreshing feel to users. No change was found with temperature change or with time, showing superior stability.

Example 19

Foundation

| (Components) | (%) |
|---|---|
| 1. M3T | 27.0 |
| 2. KF56 | 3.0 |
| 3. Glyceryl triisooctanoate | 10.0 |
| 4. KF6017 | 1.0 |
| 5. KF6026 | 1.0 |
| 5. Polyglyceryl monoisostearate | 3.0 |
| 6. Powder mixture treated for hydrophobicity* | 18.0 |
| 7. Iron oxide red | 1.2 |
| 8. Iron oxide yellow | 2.6 |
| 9. Iron oxide black | 0.2 |
| 10. 1,3-butylene glycol | 7.0 |
| 11. Sodium chloride | 0.5 |
| 12. Antiseptic | Proper quantity |
| 13. Perfume | Proper quantity |
| 14. Purified water | Balance |

*Powder mixture treated for hydrophobicity
a. Fine particle titanium dioxide 8.0
b. Fine particle zinc oxide 4.0
c. Talc 3.0
d. Mica 3.0
KF56 (produced by Shin-Etsu Chemical Co., Ltd.): Methylphenylpolysiloxane
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethyl siloxane/dimethylsiloxane copolymer (HLB = 4.7)

(Preparation Method)
A: Components a-d were mixed, to which 1% of methylhydrogenpolysiloxane was added, and then heat treated.
B: Components 1-6 were mixed and dissolved by heating and Components 7-10 were homogeneously dispersed.
C. Components 11-13 and Component 15 were mixed and then added to B to emulsify.
D. After cooling C, Component 14 was added to obtain a foundation.

The foundation thus obtained was non-sticky, evenly applicable, and well suited for the skin to give a glossy finish. It demonstrated long lasting makeup coverage. No change was found with temperature change or with time, showing superior stability.

Example 20

Hair Cream

| (Components) | (%) |
|---|---|
| 1. M3T | 10.0 |
| 2. KF56 | 5.0 |
| 3. Squalane | 4.0 |
| 4. Silicone resin | 1.0 |
| 5. Glyceryl dioleate | 2.0 |
| 6. KF6017 | 2.0 |
| 7. KF6026 | 4.0 |
| 8. Sodium sorbitol sulfate | 2.0 |
| 9. Sodium chondroitin sulfate | 1.0 |
| 10. Sodium hyaluronate | 0.5 |
| 11. Propylene glycol | 3.0 |
| 12. Antiseptic | 1.5 |
| 13. Vitamin E acetate | 0.1 |
| 14. Antioxidant | Proper quantity |
| 15. Perfume | Proper quantity |
| 16. Purified water | Balance |

KF56 (produced by Shin-Etsu Chemical Co., Ltd.): Methylphenylpolysiloxane
Silicone resin: 50% solution, in M3T, of a silicone network compound (trimethysiloxysilicate) with a ratio, [Me$_3$SiO$_{1/2}$]/[SiO$_2$], of 0.8
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethyl siloxane/dimethylsiloxane copolymer (HLB = 4.7)

(Preparation Method)
A: Components 1-7 and Components 12 and 13 were mixed while heating.
B: Components 8-11 and Component 16 were mixed to be dissolved.
C: While stirring, B was added portionwise to A to emulsify and, after cooling, Component 15 was added to obtain a hair cream.

The hair cream thus obtained was evenly applicable, moisturizing, and gave a refreshing feel to users. It maintained long lasting makeup coverage with excellent waterproofing, water repellency and sweat resistance. No change was found with temperature change or with time, showing superior stability.

Example 21

Mascara

| (Components) | (%) |
|---|---|
| 1. KP545 | 20.0 |
| 2. Dextrin palmitate/ethylhexanoate | 8.0 |
| 3. Polyethylene wax | 4.0 |
| 4. Beeswax | 7.0 |
| 5. Lecithin | 0.5 |
| 6. M3T | 22.0 |
| 7. $C_{11}$–$C_{12}$ Liquid paraffin | 20.0 |
| 8. Iron oxide | 5.0 |
| 9. AerosilRY200 | 3.5 |
| 10. Talc | 10.0 |

KP545 (produced by Shin-Etsu Chemical Co., Ltd.): Acryl silicone copolymer resin/decamethylcyclopentadiloxane 30% solution
AerosilRY200: (Nippon Aerosil Co., Ltd.) Hydrophobic silica (Preparation Method)
A: Components 1-7 were mixed to be dissolved.
B: Components 8-10 were added to A and dispersed with a roller.

The mascara thus obtained was evenly applicable, non-sticky, and gave a refreshing feel to users. It maintained long lasting makeup coverage with waterproofing, water repellency, and sweat resistance. No change was found with temperature change or with time, showing superior stability.

Example 22

Cream

| (Components) | (%) |
|---|---|
| 1. M3T | 20.0 |
| 2. Glyceryl trioctanoate | 10.0 |
| 3. KF6017 | 1.5 |
| 4. KG6026 | 4.0 |
| 5. Phenyldimethylstearyl ammonium chloride | 1.0 |
| 6. Dipropylene glycol | 10.0 |
| 7. Maltitol | 10.0 |
| 8. Saponite | 1.5 |
| 9. Antiseptic | Proper quantity |
| 10. Perfume | Proper quantity |
| 11. Purified water | Balance |

KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)

(Preparation Method)
A: Components 1-5 and 9 were mixed while heating.
B: Components 6-8 and Component 11 were dissolved by heating.
C: While stirring, B was added portionwise to A to emulsify and, after cooling, Component 10 was added to obtain a cream.

The cream thus obtained was evenly applicable, moisturizing, and gave a refreshing feel to users. It demonstrated long lasting cosmetic coverage with excellent waterproofing and water repellency. No change was found with temperature change or with time, showing superior stability.

Example 23

Cream

| (Components) | (%) |
|---|---|
| 1. M3T | 10.0 |
| 2. KF96A-6 | 5.0 |
| 3. Liquid paraffin | 5.0 |
| 4. KF6017 | 3.0 |
| 5. KF6026 | 5.0 |
| 6. Sodium citrate | 2.0 |
| 7. 1,3-butylene glycol | 5.0 |
| 8. Antiseptic | Proper quantity |
| 9. Perfume | Proper quantity |
| 10. Purified water | Balance |

KF96A-6 (produced by Shin-Etsu Chemical Co., Ltd.): Dimethylpolysiloxane with a viscosity of 6 mm²/s
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)

(Preparation Method)
A: Components 1-4 were mixed while heating.
B: Components 5-7 and Component 9 were dissolved by heating.
C: While stirring, B was added portionwise to A to emulsify and, after cooling, Component 8 was added to obtain a cream.

The cream thus obtained was evenly applicable, moisturizing, and gave a refreshing feel to users. It demonstrated long lasting cosmetic coverage with excellent waterproofing and water repellency. No change was found with temperature change or with time, showing superior stability.

Example 24

Cream

| (Components) | (%) |
|---|---|
| 1. M3T | 20.0 |
| 2. Liquid paraffin | 5.0 |
| 3. KF615A | 1.0 |
| 4. Magensium L-ascorbate phosphate | 3.0 |
| 5. Dipropylene glycol | 5.0 |
| 6. Glycerin | 5.0 |
| 7. Antiseptic | Proper quantity |
| 8. Perfume | Proper quantity |
| 9. Purified water | Balance |

KF615A (produced by Shin-Etsu Chemical Co., Ltd.): Polyoxyethylene/polyoxypropylene/methylpolysiloxane copolymer (HLB = 14.0)

(Preparation Method)
A: Components 1-3 were mixed homogeneously.
B: Components 5-7 were heated to obtain a homogeneous mixture.
C: Components 4 and 9 were dissolved homogeneously.

D: While stirring, B was added portionwise to A, and C was further added to emulsify. Then, Component 8 was added to obtain a cream.

The cream thus obtained was evenly applicable, moisturizing, well suited for the skin, and gave a fine silky look and a refreshing feel to users. It exhibited an excellent whitening effect and superior stability with no change with temperature or with time.

Example 25

Cream

| (Components) | (%) |
| --- | --- |
| 1. M3T | 20.0 |
| 2. KF56 | 5.0 |
| 3. KF6012 | 1.0 |
| 4. Dextrin fatty acid ester | 1.0 |
| 5. Glycerin | 5.0 |
| 6. Sodium chloride | 1.0 |
| 7. Antiseptic | Proper quantity |
| 8. Perfume | Proper quantity |
| 9. Purified water | Balance |

KF65 (produced by Shin-Etsu Chemical Co., Ltd.): Methylphenylpolysiloxane
KF6012 (produced by Shin-Etsu Chemical Co., Ltd.): Polyoxyethylene/polyoxypropylene/methylpolysiloxane copolymer (HLB = 7.0)

(Preparation Method)
A: Components 1-4 were mixed while heating.
B: Components 5-7 and Component 9 were dissolved by heating.
C: While stirring, B was added portionwise to A to emulsify and, after cooling, Component 8 was added to obtain a cream.

The cream thus obtained was non-sticky, evenly applicable, moisturizing, gave a fine silky look and a refreshing feel to users. It demonstrated long lasting cosmetic coverage with excellent waterproofing and sweat resistance, so that the effect of UV-ray protection continued long. No change was found with temperature change or with time, showing superior stability.

Example 26

Cream

| (Components) | (%) |
| --- | --- |
| 1. M3T | 18.0 |
| 2. KF96A-100 | 2.0 |
| 3. Polypropylene glycol (3) myristylether | 0.5 |
| 4. KF6017 | 1.4 |
| 5. KF6026 | 2.5 |
| 6. Fine particle titanium dioxide treated for hydrophobicity* | 1.0 |
| 8. Glycerin | 3.0 |
| 9. 70% sorbitol | 5.0 |
| 10. Citric acid | 25.0 |
| 11. Sodium chloride | 0.6 |
| 12. Antiseptic | Proper quantity |
| 13. Perfume | Proper quantity |
| 14. 32% aqueous ammonia | 4.5 |
| 15. Purified water | Balance |

KF96A-100 (produced by Shin-Etsu Chemical Co., Ltd.): Dimethylpolysiloxane with a viscosity of 100 mm$^2$/s
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)
*Fine particle titanium dioxode treated with aluminum stearate (Preparation Method)
A: Components 1-5 and 12 were mixed, and then Component 6 was mixed by stirring.
B: Components 7-11 and Components 13-14 were dissolved homogeneously.
C: B was added portionwise to A to emulsify to obtain a cream.

The cream thus obtained demonstrated smooth applicability with non-stickiness despite the presence of the large quantity of citric acid. No change was found with temperature change or with time, showing superior stability.

Example 27

Cream

| (Components) | (%) |
| --- | --- |
| 1. M3T | 16.0 |
| 2. KF96A-6 | 4.0 |
| 3. KF6012 | 5.0 |
| 4. POE(5) octyldodecyl ether | 1.0 |
| 5. Polyoxyethylene sorbitan monostearate (20E.O.) | 0.5 |
| 6. SUNSPHERE SZ-5 | 2.0 |
| 7. Silicone-treated fine particle titanium dioxide | 10.0 |
| 8. Liquid paraffin | 2.0 |
| 9. Macademian nut oil | 1.0 |
| 10. *Scuttellaria* Root Extract* | 1.0 |
| 11. *Gentiana* Extract** | 0.5 |
| 12. Ethanol | 5.0 |
| 13. 1,3-butylene glycol | 2.0 |
| 14. Antiseptic | Proper quantity |
| 15. Perfume | Proper quantity |
| 16. Purified water | Balance |

KF96A-6 (produced by Shin-Etsu Chemical Co., Ltd.): Dimethylpolysiloxane with a viscosity of 6 mm$^2$/s
KF6012 (produced by Shin-Etsu Chemical Co., Ltd.): Polyoxyethylene/polyoxypropylene/methylpolysiloxane copolymer (HLB = 7.0)
SUNSPHERE SZ-5 (Produced by Asahi Glass Company): Silica with a particle size ranging from 0.01 to 10 μm, encapsulating 50% of anhydrous silicic acid-treated zinc oxide
*Scuttellaria* Root Extract: extracted with a 50% aqueous 1,3-butylene glycol solution
**Gentiana* Extract: extracted with a 20% aqueous ethanol solution (Preparation Method)
A: Components 6-9 were mixed to be dispersed homogeneously.
B: Components 1-5 were mixed and A was added thereto.
C: Components 10-14 and Component 16 were mixed, to which B was added to emulsify.

D: After cooling C, Component 15 was added to obtain a cream.

The cream thus obtained was non-sticky, evenly applicable, well suited for the skin, and gave a glossy finish. It maintained long lasting cosmetic coverage. Further, no change was found with temperature change or with time, showing superior stability.

Example 28

Handcream

| (Components) | (%) |
|---|---|
| 1. M3T | 12.0 |
| 2. Liquid paraffin | 10.0 |
| 3. Silicone resin | 5.0 |
| 4. KF6017 | 1.9 |
| 5. KF6026 | 4.0 |
| 6. Distearyldimethyl ammonium chloride | 0.8 |
| 7. Vitamin E acetate | 0.1 |
| 8. Polyethylene glycol 4000 | 1.0 |
| 9. Glycerin | 10.0 |
| 10. Smectite | 1.2 |
| 11. Antiseptic | Proper quantity |
| 12. Perfume | Proper quantity |
| 13. Purified water | Balance |

Silicone resin: 70% solution, in M3T, of a silicone network compound (trimethysiloxysilicate) with a ratio, $[Me_3SiO_{1/2}]/[SiO_2]$, of 0.15
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)

(Preparation Method)

A: Components 1-7 and Component 11 were mixed while heating.

B: Components 8-10 and Component 13 were mixed under heating to be dissolved.

C: While stirring, B was added portionwise to A to emulsify and, after cooling, Component 12 was added to obtain a handcream.

The handcream thus obtained was evenly applicable, moisturizing, and gave a refreshing feel to users. It maintained long lasting makeup coverage with excellent waterproofing and water repellency. No change was found with temperature change or with time, showing superior stability.

Example 29

Handcream

| (Components) | (%) |
|---|---|
| 1. M3T | 30.0 |
| 2. Liquid paraffin | 10.0 |
| 3. Amino-modified silicone gum | 15.0 |
| 4. KF6017 | 4.0 |
| 5. Distearyldimethyl ammonium chloride | 0.8 |
| 6. Vitamin E acetate | 0.1 |
| 7. Polyethylene glycol 4000 | 1.0 |
| 8. Glycerin | 10.0 |
| 9. Smectite | 1.2 |

-continued

| (Components) | (%) |
|---|---|
| 10. Antiseptic | Proper quantity |
| 12. Perfume | Proper quantity |
| 13. Purified water | Balance |

Amino-modified silicone gum: Amine equivalence of 70000 g/mol
KF6017 (produced by Shin-Etsu Chemical Co., Ltd.): Polyoxyethylene/methylpolysiloxane copolymer (HLB = 4.6)

(Preparation Method)

A: Components 1 and 3 were heated and mixed to be dissolved, and then Components 2, 4-6 and 10 were added while heating.

B: Components 7-9 and Component 12 were mixed while heating.

C: B was added portionwise to A to emulsify and, after cooling, Component 11 was added to obtain a handcream.

The handcream thus obtained was non-sticky, evenly applicable, and gave a refreshing feel to users. It protected the skin effectively from kitchen work and also demonstrated superior stability against temperature change.

Example 30

Handcream (O/W)

| (Components) | (%) |
|---|---|
| 1. KP545 | 5.0 |
| 2. M3T | 5.0 |
| 3. KSG16 | 2.0 |
| 4. Isoparaffin | 5.0 |
| 5. Vaseline | 5.0 |
| 6. Glyceryl triisooctanoate | 3.0 |
| 7. KF6017 | 0.5 |
| 8. Polyoxyethylene sorbitan monooleate | 1.0 |
| 9. Sepigel 305 | 2.0 |
| 10. 1,3-butylene glycol | 5.0 |
| 11. Glycerin | 5.0 |
| 12. Antiseptic | Proper quantity |
| 13. Perfume | Proper quantity |
| 14. Purified water | Balance |

KP545 (produced by Shin-Etsu Chemical Co., Ltd.): 30% solution of acrylic silicone copolymer resin/decamethylcyclopentasiloxane
KSG16 (produced by Shin-Etsu Chemical Co., Ltd.): Crosslinked dimethylpolysiloxane/dimethylpolysiloxane
KF6017 (produced by Shin-Etsu Chemical Co., Ltd.): Polyoxyethylene/methylpolysiloxane copolymer (HLB = 4.6)
Sepigel 305: Light liquid paraffin (produced by SEPPIC Inc.)

(Preparation Method)

A: Components 1-7 were mixed homogeneously.

B: Components 8-11 and Component 13 were mixed homogeneously.

C: B was added to A to emulsify and Component 12 was added to obtain an O/W handcream.

The handcream thus obtained was non-sticky, evenly applicable, well suited for the skin, and gave a glossy finish. The cosmetic coverage lasted long and superior stability was obtained with no change with temperature change or with time.

Example 31

Handcream (O/W)

| (Components) | (%) |
| --- | --- |
| 1. KP545 | 5.0 |
| 2. M3T | 5.0 |
| 3. KP561 | 8.0 |
| 4. Cetanol | 1.0 |
| 5. Glyceryl triisostearate | 5.0 |
| 6. Stearic acid | 3.0 |
| 7. Glyceryl monostearate | 1.5 |
| 8. KF6015 | 0.7 |
| 9. Sorbitan sesquioleate | 0.5 |
| 10. Polyoxyethylene sorbitan monooleate | 1.0 |
| 11. Sodium hydroxide (1% aqueous solution) | 10.0 |
| 12. 1,3-butylene glycol | 5.0 |
| 13. Antiseptic | Proper quantity |
| 14. Perfume | Proper quantity |
| 15. Purified water | Balance |

KP545 (produced by Shin-Etsu Chemical Co., Ltd.): 30% solution of acrylic silicone copolymer resin/decamethylcyclopentasiloxane
KF6015 (produced by Shin-Etsu Chemical Co., Ltd.): Polyoxyethylene/methylpolysiloxane copolymer (HLB = 4.5)
KP561 (produced by Shin-Etsu Chemical Co., Ltd.): Acrylic silicone copolymer resin: stearyl-modified acrylate silicone (Preparation Method)

A: Components 1-9 were mixed and dissolved by heating.

B: Components 10-12 and Component 14 were mixed and heated.

C: B was added to A to emulsify and Component 13 was added to obtain an O/W handcream.

The handcream thus obtained was non-sticky, evenly applicable, well suited for the skin, and gave a glossy finish. It demonstrated long lasting cosmetic coverage. No change was found with temperature change or with time, showing superior stability.

Example 32

Moisturizing Cream

| (Components) | (%) |
| --- | --- |
| 1. M3T | 10.0 |
| 2. KF56 | 3.0 |
| 3. Liquid paraffin | 5.0 |
| 4. Pentaerythritol tetra-2-ethylhexanoate | 3.0 |
| 5. Cetyl 2-ethylhexanoate | 5.0 |
| 6. KF6017 | 1.0 |
| 7. KMP594 | 2.5 |
| 8. Aerosil R972 | 2.0 |
| 9. Zinc stearate | 2.0 |
| 10. Vitamin E acetate | 3.0 |
| 11. Polyoxyethylene glycol 400 | 1.0 |
| 12. Sodium lactate | 1.0 |
| 13. 1,3-butylene glycol | 5.0 |
| 14. Antiseptic | Proper quantity |
| 15. Perfume | Proper quantity |
| 16. Purified water | Balance |

KF56 (produced by Shin-Etsu Chemical Co., Ltd.): Methylphenylpolysiloxane
KF6017 (produced by Shin-Etsu Chemical Co., Ltd.): Polyoxyethylene/methylpolysiloxane copolymer (HLB = 4.6)
KMP594 (produced by Shin-Etsu Chemical Co., Ltd.): Spherical silicone elastomer resin powder
Aerosil R972 (produced by Nippon Aerosil Corp.): Hydrophobic silica (Preparation Method)

A: Components 1-6 and Components 9-10 were mixed homogeneously and Components 7-8 were dispersed homogeneously.

B: Components 11-14 and Component 16 were added to be dissolved.

C: B was added portionwise to A to emulsify and after cooling, Component 15 was added to obtain a moisturizing cream.

The moisturizing cream thus obtained was evenly applicable, moisturizing, non-sticky, and presented no changes with temperature change or time, showing superior stability and user satisfaction.

Example 33

Aftershave Cream

| (Components) | (%) |
| --- | --- |
| 1. M3T | 35.0 |
| 2. KF6017 | 2.9 |
| 3. KF6026 | 5.0 |
| 4. Polyethylene glycol (molecular weight: 400) | 5.0 |
| 5. Sodium L-glutamate | 2.0 |
| 6. Arantoin | 0.1 |
| 7. Aloe extract | Proper quantity |
| 8. Antiseptic | Proper quantity |
| 9. Antioxidant | Proper quantity |
| 10. Perfume | Proper quantity |
| 11. Purified water | Balance |

KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleymethylsilicone/dimethylsiloxane copolymer (HLB = 4.7)

(Preparation Method)

A: Components 1-4 and Components 10 and 11 were mixed while heating.

B: Components 5-9 were mixed while heating.

C: B was added portionwise to A to emulsify to obtain an aftershave cream.

The aftershave cream thus obtained was evenly applicable and not sticky, and did not drip since it was highly viscous. It maintained a moisturizing feel after the application and demonstrated very high stability.

Example 34

Eye Wrinkle Cream

| (Components) | (%) |
| --- | --- |
| 1. M3T | 20.0 |
| 2. KF7312J | 5.0 |
| 3. KF6017 | 2.0 |
| 4. KF6026 | 5.0 |
| 5. Sodium chondroitin sulfate | 2.0 |
| 6. Sodium lactate | 1.0 |
| 7. Glycerin | 50.0 |
| 8. Antiseptic | Proper quantity |
| 9. Antioxidant | Proper quantity |
| 10. Perfume | Proper quantity |
| 11. Purified water | Balance |

KF7312J (produced by Shin-Etsu Chemical Co., Ltd.): Silicone resin: 50% solution in decamethylcyclopentasiloxane, of a silicone network compound (trimethylsiloxysilicate) with a ratio, [Me$_3$SiO$_{1/2}$]/[SiO$_2$], of 0.8
KF6017 (produced by Shin-Etsu Chemical Co., Ltd.): Polyoxyethylene/methylpolysiloxane copolymer (HLB = 4.6)
KF6026 (produced by Shin-Etsu Chemical Co., Ltd.): Polyoxyethylenemethylsiloxane/polyoxypropyleneoleymethylsilicone/dimethylsiloxane copolymer (HLB = 4.7)

(Preparation Method)

A: Components 1-4 and Component 9 were mixed while heating.

B: Components 5-8 and Component 11 were dissolved by heating.

C: While stirring, B was added portionwise to A to emulsify and, after cooling, Component 10 was added to obtain an eye wrinkle cream.

The eye wrinkle cream thus obtained was evenly applicable, moisturizing, and gave a refreshing feel to users. It maintained long lasting cosmetic coverage. No change was found with temperature change or with time, showing superior stability.

Example 35

Eyeshadow

| (Components) | (%) |
| --- | --- |
| 1. M3T | 15.0 |
| 2. KF96A-6 | 10.0 |
| 3. KF6012 | 2.0 |
| 4. PEG(10) laurylether | 0.5 |
| 5. Silicone-treated chromium oxide* | 6.2 |
| 6. Silicone-treated ultramarine blue* | 4.0 |
| 7. Silicone-treated titanium-coated mica* | 6.0 |
| 8. Sodium chloride | 2.0 |
| 9. Propylene glycol | 8.0 |
| 10. Antiseptic | Proper quantity |
| 11. Perfume | Proper quantity |
| 12. Purified water | Balance |

KF96A-6 (produced by Shin-Etsu Chemical Co., Ltd.): Dimethylpolysiloxane with a viscosity of 6 mm$^2$/s
KF6012 (produced by Shin-Etsu Chemical Co., Ltd.): Polyoxyethylene/polyoxypropylene/methylpolysiloxane copolymer (HLB = 7.0)
*Silicone treatment: 3%, based on the powder, of methylhydrogenpolysiloxane was added to the powder, followed by neat treatment.

(Preparation Method)

A: Components 1-4 were mixed, to which Component 5-7 were added and dispersed homogeneously.

B: Components 8-10 and Component 12 were dissolved homogeneously.

C: While stirring, B was added portionwise to A to emulsify and Component 11 was added to obtain an eyeshadow.

The eyeshadow thus obtained was evenly applicable, moisturizing without an oily look or a powdery look, and gave a refreshing feel to users. It maintained satisfactory makeup coverage with excellent waterproofing, water repellency and sweat resistance, and did not cause makeup-run. No change was found with temperature change or with time, showing superior stability.

Example 36

Eyeliner

| (Components) | (%) |
| --- | --- |
| 1. M3T | 22.0 |
| 2. KF96A-6 | 5.0 |
| 3. Jojoba oil | 2.0 |
| 4. KF6017 | 1.0 |
| 5. Silicone-treated iron oxide black (Note) | 20.0 |
| 6. Ethanol | 5.0 |
| 7. Antiseptic | Proper quantity |
| 8. Purified water | Balance |

KF96A-6 (produced by Shin-Etsu Chemical Co., Ltd.): Dimethylpolysiloxane with a viscosity of 6 mm$^2$/s
KF6017 (produced by Shin-Etsu Chemical Co., Ltd.): Polyoxyethylene/methylpolysiloxane copolymer (HLB = 4.6)
(Note)
Silicone-treated Iron oxide black: 2% of methylhydrogenpolysiloxane was added to iron oxide black, followed by heat treatment.

(Preparation Method)

A: Components 1-4 were mixed while heating, to which Component 5 was added to be dispersed homogeneously.

B: Components 6-8 were dissolved by heating.

C: While stirring, B was added portionwise to A to emulsify to obtain an eyeliner.

The eyeliner thus obtained demonstrated a light touch and easy drawing when applied, a moisturizing feel without an oily look or a powdery look, and gave a refreshing feel to users. It maintained long lasting cosmetic effect with excellent waterproofing, water repellency and sweat resistance not to cause makeup-run. No change was found with temperature change or with time, showing superior stability.

Example 37

Eyeliner

| (Components) | (%) |
|---|---|
| 1. M3T | 22.0 |
| 2. KF96A-6 | 5.0 |
| 3. Silicone-treated iron oxide black | 20.0 |
| 4. Vitamin E acetate | 0.2 |
| 5. Jojoba oil | 2.0 |
| 6. Bentonite | 3.0 |
| 7. KF6012 | 2.0 |
| 8. Ethanol | 10.0 |
| 9. 1,3-butylenle glycol | 10.0 |
| 10. Antiseptic | Proper quantity |
| 11. Perfume | Proper quantity |
| 12. Purified water | Balance |

KF96A-6 (produced by Shin-Etsu Chemical Co., Ltd.): Dimethylpolysiloxane with a viscosity of 6 mm$^2$/s
KF6012 (produced by Shin-Etsu Chemical Co., Ltd.): Polyoxyethylene/polyoxypropylene/methylpolysiloxane copolymer (HLB = 7.0)

(Preparation Method)
A: Components 1, 2, and 4-7 were mixed, to which Component 3 was added to be dispersed homogeneously.
B: Components 8-10 and Component 12 were mixed.
C: B was added portionwise to A to emulsify and, after cooling, Component 11 was added to obtain an eyeliner.

The eyeliner thus obtained demonstrated a light touch and ease in drawing, and gave a refreshing feel to users. No change was found with temperature change or with time, showing superior stability and user satisfaction. It maintained long lasting cosmetic coverage with excellent waterproofing and sweats resistance.

Example 38

Antiperspirant

| (Components) | (%) |
|---|---|
| 1. M3T | 30.0 |
| 2. KF6026 | 1.0 |
| 3. Polyoxyethylenesorbitan monooleate (20 E.O.) | 0.5 |
| 6. Aluminum zirconium tetrachlorohydrate glycine salt | 20.0 |
| 8. Purified water | Balance |

KF6026 (produced by Shin-Etsu Chemical Co., Ltd.): Polyoxyethylenemethylsiloxane/polyoxypropyleneoleymethylsilicone/dimethylsiloxane copolymer (HLB = 4.7)

(Preparation Method)
A: Components 1 and 2 were mixed.
B: Component 4 was dissolved in Component 5, and Component 3 was added.
C: While stirring, B was added portionwise to A to emulsify to obtain an antiperspirant.

The antiperspirant thus obtained was evenly applicable, non-sticky, did not leave too much white powdery residue, and gave a refreshing feel to users. No change was found with temperature change or with time, showing superior stability.

Example 39

Antiperspirant

| (Components) | (%) |
|---|---|
| 1. KSG-21 | 20.0 |
| 2. KSG-15 | 20.0 |
| 3. M3T | 30.0 |
| 4. Aluminum zirconium tetrachlorohydrate [Aluminum Zirconium Tetrachlorohydrex GLY] | 20.0 |
| 5. KF-96A-6 | 10.0 |

KSG21 (produced by Shin-Etsu Chemical Co., Ltd.): Crosslinked polyether-modified methylpolysiloxane/dimethylpolysiloxane
KSG15 (produced by Shin-Etsu Chemical Co., Ltd.): Crosslinked polyether-modified methylpolysiloxane/decamethylcyclopentasiloxane
KF96A-6 (produced by Shin-Etsu Chemical Co., Ltd.): Dimethylpolysiloxane with a viscosity of 6 mm$^2$/s (Preparation Method)
A: Components 1-3 and Component 5 were mixed homogeneously.
B: Component 4 was added to A and dispersed by mixing.

The antiperspirant thus obtained was non-sticky and evenly applicable. It showed superior stability with no change with temperature change or with time.

Example 40

Transparent Gel Cosmetic

| (Components) | (%) |
|---|---|
| 1. M3T | 10.0 |
| 2. KF615A | 10.0 |
| 3. 1,3-butylene glycol | 10.0 |
| 4. Polyethylene glycol 400 | 9.0 |
| 5. 2-hydroxyoctanoic acid | 1.0 |
| 6. Sorbitol (70% aqueous solution) | 10.0 |
| 7. Citric acid | Proper quantity |
| 8. Sodium citrate | Proper quantity |
| 9. Antiseptic | Proper quantity |
| 10. Perfume | Proper quantity |
| 11. Purified water | Balance |

KF615A (produced by Shin-Etsu Chemical Co., Ltd.): Polyoxyethylene/polyoxypropylene/methylpolysiloxane copolymer (HLB = 14.0)

(Preparation Method)
A: Components 3-11 were dissolved homogeneously.
B: Components 1 and 2 were mixed to obtain a homogeneous mixture.
C: While stirring, A was added portionwise to B to emulsify to obtain a transparent gel cosmetic.

The transparent gel cosmetic thus obtained was evenly applicable, moisturizing, well suited for the skin, and gave a refreshing feel to users. It demonstrated superior stability with no change with temperature change or with time.

Example 41

Milky Lotion

| (Components) | (%) |
| --- | --- |
| 1. M3T | 18.0 |
| 2. KF96A-6 | 6.0 |
| 3. Squalan | 5.0 |
| 4. Neopentylglycol dioctanoate | 3.0 |
| 5. α-monooleylglyceryl ether | 1.0 |
| 6. KF6017 | 2.0 |
| 7. Aluminum distearate | 0.2 |
| 8. Magnesium sulfate | 0.7 |
| 9. Glycerin | 5.0 |
| 10. Antiseptic | Proper quantity |
| 10. Perfume | Proper quantity |
| 11. Purified water | Balance |

KF96A-6 (produced by Shin-Etsu Chemical Co., Ltd.): Dimethylpolysiloxane with a viscosity of 6 mm$^2$/s
KF6017 (produced by Shin-Etsu Chemical Co., Ltd.): Polyoxyethylene/methylpolysiloxane copolymer (HLB = 4.6)

(Preparation Method)

A: Components 1-7 were mixed while heating.

B: Components 8-10 and Component 12 were dissolved while heating.

C: While stirring, B was added portionwise to A and, after cooling, Component 11 was added to obtain a milky lotion.

The milky lotion thus obtained had a low viscosity to present a silky look, evenly applicable, and gave a refreshing feel to users. It maintained satisfactory cosmetic coverage and superior stability with no change with temperature change or with time.

Example 42

Milky Lotion

| (Components) | (%) |
| --- | --- |
| 1. M3T | 15.0 |
| 2. KF96A-6 | 6.0 |
| 3. Squalan | 5.0 |
| 4. Neopentylglycol dioctanoate | 3.0 |
| 5. α-monooleylglyceryl ether | 1.0 |
| 6. KF6026 | 1.5 |
| 7. KF6017 | 1.0 |
| 8. Aluminum distearate | 0.2 |
| 9. Dextrin fatty acid ester | 1.0 |
| 10. Magnesium sulfate | 0.7 |
| 11. Glycerin | 5.0 |
| 12. Antiseptic | Proper quantity |
| 13. Perfume | Proper quantity |
| 14. Purified water | Balance |

KF96A-6 (produced by Shin-Etsu Chemical Co., Ltd.): Dimethylpolysiloxane with a viscosity of 6 mm$^2$/s
KF6026 (produced by Shin-Etsu Chemical Co., Ltd.): Polyoxyethylenemethylsiloxane/polyoxypropyleneoleylmethylsiloxane/dimethylsiloxane copolymer (HLB = 4.7)
KF6017 (produced by Shin-Etsu Chemical Co., Ltd.): Polyoxyethylene/methylpolysiloxane copolymer (HLB = 4.6)

(Preparation Method)

A: Components 1-9 were mixed while heating.

B: Components 10-12 and Component 14 were dissolved while heating.

C: While stirring, B was added portionwise to A to emulsify and, after cooling, Component 13 was added to obtain a milky lotion.

The milky lotion thus obtained had a low viscosity to present a silky look, evenly applicable, and gave a refreshing feel to users. It maintained satisfactory cosmetic coverage and superior stability with no change with temperature change or with time.

Example 43

Milky Lotion

| (Components) | (%) |
| --- | --- |
| 1. M3T | 15.0 |
| 2. KF56 | 5.0 |
| 3. Squalane | 5.0 |
| 4. Pentaneerythritol tetra-2-ethylhexanoate | 5.0 |
| 5. KF6017 | 3.0 |
| 6. KMP594 | 2.0 |
| 7. Aerosil R972 | 0.5 |
| 8. Magnesium ascorbate phosphate | 1.0 |
| 9. Sodium chloride | 1.0 |
| 10. Polyethylene glycol 11000 | 1.0 |
| 11. Propylene glycol | 8.0 |
| 12. Antiseptic | Proper quantity |
| 13. Perfume | Proper quantity |
| 14. Purified water | Balance |

KF56 (produced by Shin-Etsu Chemical Co., Ltd.): Methylphenylpolysiloxane
KF6017 (produced by Shin-Etsu Chemical Co., Ltd.): Polyoxyethylene/methylpolysiloxane copolymer (HLB = 4.6)
KMP594 (produced by Shin-Etsu Chemical Co., Ltd.): Spherical silicone elastomer resin powder
Aerosil R972 (produced by Nippon Aerosil Co., Ltd.): Hydrophobic silica (Preparation Method)

A: Components 1-5 were mixed homogeneously, to which Components 6 and 7 were added to disperse homogeneously.

B: Components 8-10 were added to Component 14 to be dissolved. Components 11 and 12 were mixed with each other homogeneously and added to the solution.

C: B was added portionwise to A to emulsify and, after cooling, Component 13 was added to obtain a milky lotion.

The milky lotion thus obtained was non-sticky and evenly applicable. No change was found with temperature change or with time, showing superior stability.

Example 44

Beautifying Liquid

| (Components) | (%) |
|---|---|
| 1. M3T | 12.0 |
| 2. Glyceryl triisooctanoate | 10.0 |
| 3. KF6017 | 2.0 |
| 4. KSG21 | 0.2 |
| 5. Glycerin | 10.0 |
| 6. Magnesium ascorbate phosphate | 3.0 |
| 7. Sodium chloride | 2.0 |
| 8. Antiseptic | Proper quantity |
| 9. Perfume | Proper quantity |
| 10. Purified water | Balance |

KF6017 (produced by Shin-Etsu Chemical Co., Ltd.): Polyoxyethylene/methylpolysiloxane copolymer (HLB = 4.6)
KSG21 (produced by Shin-Etsu Chemical Co., Ltd.): Crosslinked polyether-modified methylpolysiloxane/dimethylpolysiloxane (Preparation Method)
A: Components 1-4 were mixed while heating.
B: Components 5-8 and Component 10 were heated to be dissolved homogeneously.
C: While stirring, B was added portionwise to A to emulsify and, after cooling, Component 9 was added to obtain a beautifying liquid.

The beautifying liquid thus obtained demonstrated a fine silky look with excellent applicability and a moisturizing effect. No change was found with temperature change or with time, showing superior stability.

Example 45

Deodorant

| (Components) | (%) |
|---|---|
| 1. M3T | 12.0 |
| 2. KF96A-6 | 4.0 |
| 3. KF615A | 1.0 |
| 4. Propylene glycol | 31.0 |
| 5. Triclosan | 0.1 |
| 6. Glycerin | 15.0 |
| 7. Antiseptic | Proper quantity |
| 8. Perfume | Proper quantity |
| 9. Purified water | Balance |

KF96A-6 (produced by Shin-Etsu Chemical Co., Ltd.): Dimethylpolysiloxane with a viscosity of 6 mm²/s
KF615A (produced by Shin-Etsu Chemical Co., Ltd.): Polyoxyethylene/polyoxypropylene/methylpolysiloxane copolymer (HLB = 14.0)

(Preparation Method)
A: Components 1-3 were mixed.
B: Components 5 was dissolved in Component 4, and then Components 6-9 were mixed.
C: B was added to A to emulsify while vigorous stirring.

D: 65 parts of C and 35 parts of a propellant(mixture of n-butane, isobutene, and propane) were put in an aerosol can to obtain a deodorant.

The deodorant thus obtained demonstrated no dripping when used at a high concentration and non-stickiness. It gave a high user satisfaction, providing a long lasting effect.

Example 46

Aerosol Composition (Astringent-Deodorant)

| (Components) | (%) |
|---|---|
| 1. Silicone-treated mica | 3.0 |
| 2. Chlorohydroxyaluminum | 2.0 |
| 3. Isopropylmethylphenol | 0.3 |
| 4. Sorbitan sesquioleate | 0.2 |
| 5. Isopropylmyristate | 5.0 |
| 6. M3T | 5.0 |
| 7. Perfume | Proper quantity |
| 8. Propellant | Balance |

(Preparation Method)
A: Components 1-7 were mixed.
B: After putting A in an aerosol can, Component 8 was filled.

The-aerosol composition of the present invention thus obtained demonstrated a high deodorizing effect, no stickiness when applied and a satisfactory even applicability with a smooth feel to the touch. Furthermore, it demonstrated excellent user satisfaction on account of high re-dispersability.

INDUSTRIAL APPLICABILITY

As described above, the cosmetic of the present invention demonstrates high volatility and an excellent feel to the touch since it contains M3T. Furthermore, the cosmetic of the present invention does not cause a defatting action on the skin, so that it shows superior stability.

The invention claimed is:
1. A method of reducing dry feel associated with cyclic silicone in a cosmetic, comprising the step of applying to the skin a cosmetic comprising an organopolysiloxane expressed byte following general formula (1)

$$\{(CH_3)_3SiO\}_3SiCH_3 \qquad (1),$$

and at least one cyclic silicone selected from the group consisting of octamethylcyclotetrasiloxane, decarnethylcyclopentasiloxane, and dodecamethylcyclohexasiloxane in a mass ratio of the organopolysiloxane to the cyclic silicone of from 99:1 to 1:99.

2. The method as described in claim 1, wherein the cosmetic further contains at least one other kind of organopolysiloxane than that of the formula (1) and the cyclic silicone.

3. The method as described in claim 2, wherein said other kind of organopolysiloxane is liquid at 25° C. and 1 atm.

4. The method as described in claim 3, wherein said liquid organopolysiloxane is volatile at 25° C. and 1 atm.

5. The method as described in claim 3, wherein said liquid organopolysiloxane is non-volatile at 25° C. and 1 atm.

6. The method as described in claim 5, wherein said non-volatile organopolysiloxane is at least one selected from the group consisting of dimethylpolysiloxanes and methylphenylpolysiloxanes.

7. The method as described in claim 2, wherein said other kind of organopolysiloxane is of a form of paste, gum, elastomeric solid or non-elastomeric solid at 25° C. and 1 atm.

8. The method as described in claim 7, wherein said gum form of organopolysiloxane is dimethylpolysiloxane gum with a degree of polymerization ranging from 3,000 to 20,000.

9. The method as described in claim 7, wherein said elastomeric solid form or non-elastomeric solid form of organopolysiloxane is dispersed in the cosmetic.

10. The method as described in claim 9, wherein said non-elastomeric solid form of organopolysiloxane is polyalkylsilsesquioxane spherical powder.

11. The method as described in claim 10, wherein said non-elastomeric solid form of organopolysiloxane is at least one selected from the group consisting of acryl silicone copolymers, fluorinated organopolysiloxanes, trimethylsiloxysilicates (i.e., MQ resins), and trimethylsiloxysilicates containing a dimethylsiloxy group (i.e., MDQ resins).

12. The method as described in claim 2, wherein said other kind of organopolylsiloxane is a modified organopolysiloxane.

13. The method as described in claim 12, wherein said modified organopolysiloxane is at least one selected from the group consisting of fluorinated organopolysiloxanes, polyether-modified organopolysiloxanes, amino-modified organopolysiloxanes, organopolysiloxanes containing an alcoholic hydroxyl group, glyceryl-modified organopolysiloxanes, and polyglyceryl-modified organopolysiloxanes.

14. The method as described in claim 2, wherein said other kind of organopolysiloxanes is a crosslinked type organopolysiloxane.

15. The method as described in claim 14, wherein said crosslinked organopolysiloxane is a reaction product of organopolysiloxane having at least two alkenyl groups per molecule with organohydrogenpolysiloxane having a Si—H bond.

16. The method as described in claim 14, wherein said crosslinked organopolysiloxane has at least one moiety selected from the group consisting of polyoxyalkylene moieties, alkyl moieties, alkenyl moieties, and aryl moieties.

17. The method as described in claim 14, wherein said crosslinked organopolysiloxane is contained in the cosmetic in a state swollen in an organopolysiloxane of a dynamic viscosity of 0.65 to 100 mm$^2$/s.

18. The method as described in claim 1, wherein the cosmetic further contains at least one component selected from the group consisting of fluorine-containing compound, a UV-ray protective component, a compound having an alcoholic hydroxyl group, and a thickening agent.

19. The method as described in claim 18, wherein said UV-ray protective component is at least one selected from the group consisting of titanium oxide fine particle, zinc oxide fine particle, 2-ethylhexyl paramethoxycinnamate, 4-tert-butyl-4'methoxydibenzoylmethane, and benzophenone UV-ray absorbents.

20. The method as described in claim 1, wherein the mass ratio of the organopolysiloxane expressed by the formula (1) to the cyclic silicone ranges from 10:90 to 95:5.

* * * * *